(12) United States Patent
Nagaso et al.

(10) Patent No.: US 9,125,836 B2
(45) Date of Patent: Sep. 8, 2015

(54) FILM PREPARATION WITH RAPIDLY DISSOLVING PROPERTY AND FLEXIBILITY

(75) Inventors: Toshiro Nagaso, Shinagawa-ku (JP); Mitsutoshi Tatara, Shinagawa-ku (JP); Toshihito Shimizu, Minato-ku (JP)

(73) Assignee: SATO PHARMACEUTICAL CO., LTD., Tokyo (JP)

( * ) Notice: Subject to any disclaimer, the term of this patent is extended or adjusted under 35 U.S.C. 154(b) by 328 days.

(21) Appl. No.: 12/663,258

(22) PCT Filed: Jun. 7, 2007

(86) PCT No.: PCT/JP2007/061527
§ 371 (c)(1),
(2), (4) Date: Jan. 26, 2010

(87) PCT Pub. No.: WO2008/149440
PCT Pub. Date: Dec. 11, 2008

(65) Prior Publication Data
US 2010/0150986 A1    Jun. 17, 2010

(51) Int. Cl.
*A61K 9/70* (2006.01)
*A61K 9/00* (2006.01)
*A61K 47/38* (2006.01)

(52) U.S. Cl.
CPC ............. *A61K 9/7007* (2013.01); *A61K 9/0056* (2013.01); *A61K 47/38* (2013.01)

(58) Field of Classification Search
CPC combination set(s) only.
See application file for complete search history.

(56) References Cited

U.S. PATENT DOCUMENTS

| | | | | |
|---|---|---|---|---|
| 3,573,058 | A | * | 3/1971 | Tiemstra ...................... 426/658 |
| 6,248,357 | B1 | * | 6/2001 | Ohno et al. .................... 424/465 |
| 2003/0054034 | A1 | | 3/2003 | Leung et al. |
| 2003/0099690 | A1 | * | 5/2003 | Awamura et al. ............. 424/443 |
| 2004/0247677 | A1 | | 12/2004 | Oury et al. |
| 2005/0136112 | A1 | | 6/2005 | Gonzales et al. |
| 2005/0147653 | A1 | | 7/2005 | Yasuda et al. |
| 2005/0163830 | A1 | | 7/2005 | Rademacher et al. |
| 2007/0036861 | A1 | | 2/2007 | Oury et al. |
| 2010/0239667 | A1 | * | 9/2010 | Hemmingsen et al. ....... 424/466 |

FOREIGN PATENT DOCUMENTS

| | | |
|---|---|---|
| EP | 1 008 343 A1 | 6/2000 |
| EP | 1 752 127 A1 | 2/2007 |
| JP | 62-63513 A | 3/1987 |
| JP | 63-109865 A | 5/1988 |
| JP | 6-105660 A | 4/1994 |
| JP | 2559301 B2 | 9/1996 |
| JP | 9-235220 A | 9/1997 |
| JP | 2002-525306 A | 8/2002 |
| JP | 34060538 B2 | 8/2003 |
| JP | 2004-043450 A | 2/2004 |
| JP | 2005-21124 A | 1/2005 |
| JP | 2005-517722 A | 6/2005 |
| JP | 3730081 B2 | 12/2005 |
| JP | 2006-527184 A | 11/2006 |
| JP | 2007-514767 A | 6/2007 |
| WO | 2007/030754 A2 | 3/2007 |
| WO | 2008/112124 A2 | 9/2008 |

OTHER PUBLICATIONS www.sigmaaldrich.com ("cellulose colloidal, microcrystalline") (.pdf attached).*
Japanese Pharmaceutical Excipients Directory 2007, Yakuji Nippo Limited, 1st edition, p. 253, 2007.
European Patent Office, European Search Report issued in corresponding EP Application No. 07744857.9, dated Nov. 8, 2013.

* cited by examiner

*Primary Examiner* — Michael G Hartley
*Assistant Examiner* — Robert Cabral
(74) *Attorney, Agent, or Firm* — Sughrue Mion, PLLC

(57) ABSTRACT

The present invention relates to a film preparation having both rapid solubility and flexibility at the same time. The film preparation is characterized by comprising: an active-ingredient-containing layer comprising an active ingredient, a water-soluble polymer selected from the group consisting of methyl cellulose, hydroxypropyl cellulose, and hydroxypropyl methyl cellulose, and a disintegrating agent; and an active-ingredient-free layer comprising methyl cellulose and/or hydroxypropyl methyl cellulose. It is further characterized in that the amount of the active ingredient is 0.1-75.0 mass % of a total mass of the film preparation and a total content of the active ingredient and the water-soluble polymer in the active-ingredient-containing layer is 15.0-95.0 mass % of a total mass of the active-ingredient-containing layer.

7 Claims, No Drawings

FILM PREPARATION WITH RAPIDLY DISSOLVING PROPERTY AND FLEXIBILITY

TECHNICAL FIELD

The present invention relates to a film preparation having both rapid solubility and flexibility at the same time.

BACKGROUND ART

A film preparation made by formulating an active ingredient such as a drug and a food component into a film shape has been known to have advantages that the film preparation can be taken without water and has high solubility (rapid solubility), and so forth.

For example, the followings are known as the film preparation.

A monolayer film preparation including gelatin, pectin, glycerin and a sucrose fatty acid ester (Patent Document 1).

A monolayer film preparation including a drug, an edible polymer and a saccharide as main components (Patent Document 2).

A monolayer film preparation including a medical substance and a water soluble polymer (Patent Document 3).

A monolayer film preparation including a medical drug and hydroxypropyl cellulose (Patent Document 4).

A monolayer film preparation including a drug and pullulan (Patent Document 5).

A monolayer film preparation including a food material or the like, a pregelatinized starch and/or pullulan, and a plasticizer (Patent Document 6).

A non-rapidly-soluble multilayer film preparation including an active ingredient-containing layer whose base is a water soluble polymer and a non-adhesive layer having a poor solubility to water (Patent Document 7).

A film preparation made by laminating a coating layer a including a water-soluble and non-water-absorbing polysaccharide and a softener, a drug layer b including a drug and an edible water soluble polymer substance, and a drug layer c including a drug, an edible water soluble polymer substance and a tannin substance, in the order of a, b, c, b and a (Patent Document 8).

A monolayer film preparation including a film forming agent, a water swelling gel forming agent, an active substance, a filler and a polar solvent (Patent Document 9).

Patent Document 1: Japanese Unexamined Patent Application Publication No. Hei 6-105660
Patent Document 2: Japanese Patent No. 3460538
Patent Document 3: Published Japanese Translation of PCT Application No. 2002-525306
Patent Document 4: Japanese Unexamined Patent Application Publication No. Sho 62-63513
Patent Document 5: Japanese Unexamined Patent Application Publication No. Sho 63-109865
Patent Document 6: Japanese Unexamined Patent Application Publication No. 2005-21124
Patent Document 7: Japanese Unexamined Patent Application Publication No. Hei 9-235220
Patent Document 8: Japanese Patent No. 3730081
Patent Document 9: Japanese Patent No. 2559301

DISCLOSURE OF THE INVENTION

Problems to be Solved by the Invention

The present inventors have discovered problems of lowered film flexibility and poor usability in dosing easiness or storage stability, when a disintegrating agent is formulated in order to increase the rapid solubility of a film preparation.

Meanwhile, in the field of film preparation, the content of an active ingredient in a film is desirably high from the viewpoint of reducing the number of dosage times. For this reason, when an active ingredient is used in high content, the obtained film has a problem that the advantage in rapid solubility is impaired. Furthermore, there also is a problem of poor usability in dosing easiness or storage stability because the film containing the active ingredient in high content is easy to break due to its low flexibility.

Therefore, the present invention aims to provide a film preparation having both rapid solubility and flexibility at the same time. Furthermore, the present invention aims to provide a film preparation containing an active ingredient in high content without losing the advantage in rapid solubility of the film and with the flexibility retained.

Means for Solving the Problems

In the present invention, it has been discovered that the rapid solubility and flexibility of a film can be maintained as follows. Specifically, in preparing a film preparation, the film is separately constituted of: an active-ingredient-containing layer and an active-ingredient-free layer. A predetermined water soluble polymer and a disintegrating agent are further formulated into the active-ingredient-containing layer, and a predetermined water soluble polymer is formulated into the active-ingredient-free layer. The present invention thus achieved is based on this discovery.

Specifically, the present invention relates to:
(1) a rapidly soluble film preparation comprising:
    an active-ingredient-containing layer comprising
        an active ingredient,
        a water soluble polymer selected from the group consisting of methyl cellulose, hydroxypropyl cellulose and hydroxypropyl methyl cellulose, and
        a disintegrating agent; and
    an active-ingredient-free layer comprising
        methyl cellulose and/or hydroxypropyl methyl cellulose,
    the film preparation characterized in that a content of the active ingredient is from 0.1% by mass to 75.0% by mass of a total mass of the film preparation, and
    a total content of the active ingredient and the water soluble polymer in the active-ingredient-containing layer is from 15.0% by mass to 95.0% by mass of a total mass of the active-ingredient-containing layer;
(2) the rapidly soluble film preparation according to (1) described above, which has a three-layer structure in which the active-ingredient-free layers exist on each side of the active-ingredient-containing layer;
(3) the rapidly soluble film preparation according to (1) described above, which has a two-layer structure in which the active-ingredient-free layer exists on one side of the active-ingredient-containing layer;
(4) the rapidly soluble film preparation according to (1) described above, in which the active-ingredient-containing layer further comprises a masking reagent for the active ingredient;
(5) the rapidly soluble film preparation according to (1) described above, in which the disintegrating agent is a water-foamable disintegrating agent, and the water soluble polymer is hydroxypropyl cellulose;

(6) the rapidly soluble film preparation according to (1) described above, in which the disintegrating agent is a mixture of crystalline cellulose and carboxymethyl cellulose sodium;

(7) the rapidly soluble film preparation according to (6) described above, in which the mixture of crystalline cellulose and carboxymethyl cellulose sodium is a colloidal grade;

(8) the rapidly soluble film preparation according to (1) described above, which is a film preparation for oral administration; and (9) the film preparation according to (1) described above, in which the active ingredient is selected from the group consisting of a sedative hypnotic, an antianxiety drug, an antiepileptic, a rhinitis drug, an antipyretic-analgesic-anti inflammatory drug, an anti-parkinsonian, an antipsychotic, a local anesthetic agent, a cerebral circulation and metabolism ameliorator, an antispasmodic, an antiemetic, a cardiotonic drug, an antiarrhythmic, a diuretic, an antihypertensive, a vasoconstrictor, a vasodilator, a hypolipidemic drug, a respiratory stimulant, an antitussive, an expectorant, an antitussive and expectorant drug, a bronchodilator, a gargle, an antidiarrheal, an intestinal regulator, an antiulcer drug, a stomachic, an antacid, a laxative, a cholagogue, an analeptic, an antipodagric, a anti-diabetic drug, an antibiotic, an antimicrobial, an osteoporosis drug, a skeletal muscle relaxant, an antirheumatic agent, a hormonal drug, an alkaloidal narcotic, a blood coagulation inhibitor, an antineoplastic, an antihistaminic and an antiallergic.

Effects of the Invention

A film preparation of the present invention can have both rapid solubility and flexibility at the same time, as shown in Examples to be described below. Moreover, the film preparation of the present invention can retain the flexibility without losing the advantage in rapid solubility of the film, even when an active ingredient is formulated in high content. Consequently, the further wide use of film preparations can be achieved.

BEST MODES FOR CARRYING OUT THE INVENTION

The present invention will be described in detail below.

A film preparation of the present invention is composed of an active-ingredient-containing layer and an active-ingredient-free layer.

The active-ingredient-containing layer comprises: an active ingredient; a water soluble polymer selected from the group consisting of methyl cellulose, hydroxypropyl cellulose and hydroxypropyl methyl cellulose; and a disintegrating agent.

The active ingredient refers to a substance capable of providing some sort of effect on a living body into which a film preparation is taken. The active ingredient includes not only a drug but also a food component.

The drug used as the active ingredient is not particularly limited as long as the administration with the film preparation is possible. The drug may be in any state of solid or liquid at normal temperature. In addition, the drug may be systemically active or may be locally active.

Specific examples of the drug include sedative hypnotics, antianxiety drugs, antiepileptics, rhinitis drugs, antipyretic-analgesic-anti inflammatory drugs, anti-parkinsonians, antipsychotics, local anesthetic agents, cerebral circulation and metabolism ameliorators, antispasmodics, antiemetics, cardiotonic drugs, antiarrhythmics, diuretics, antihypertensives, vasoconstrictors, vasodilators, hypolipidemic drugs, respiratory stimulants, antitussives, expectorants, antitussive and expectorant drugs, bronchodilators, gargles, antidiarrheals, intestinal regulators, antiulcer drugs, stomachics, antacids, laxatives, cholagogues, analeptics, antipodagrics, anti-diabetic drugs, antibiotics, antimicrobials, osteoporosis drugs, skeletal muscle relaxants, antirheumatic agents, hormonal drugs, alkaloidal narcotics, blood coagulation inhibitors, antineoplastics, antihistaminics and antiallergics.

More specifically, the examples thereof include the following substances.

Sedative Hypnotics and Antianxiety Drugs
Estazolam, nitrazepam, diazepam, phenobarbital, alprazolam and chlordiazepoxide Antiepileptics
Phenytoin, carbamazepine and sodium valproate Antipyretic-analgesic-anti Inflammatory Drugs
Aspirin, acetaminophen, ethenzamide, ibuprofen, lysozyme chloride, mefenamic acid, diclofenac sodium, ketoprofen, indomethacin, phenacetin and caffeine Anti-parkinsonians
Amantadine hydrochloride, levodopa and trihexyphenidyl hydrochloride Antipsychotics
Sulpiride, haloperidol, chlorpromazine, reserpine, risperidone and fluvoxamine maleate Local Anesthetics
Procaine and lidocaine Cerebral Circulation and Metabolism Ameliorator
Meclophenoxate hydrochloride, nicergoline and taltirelin Antispasmodics
Scopolamine hydrobromide, papaverine hydrochloride, atropine sulfate and propantheline bromide Antiemetics
Difenidol hydrochloride, dimenhydrinate, meclizine hydrochloride, chlorpheniramine d-maleate and scopolamine hydrobromide Cardiotonic Drugs
Digoxin, ubidecarenone, etilefrine hydrochloride and dopamine hydrochloride Antiarrhythmics
Mexiletine hydrochloride, propranolol hydrochloride, pindolol and atenolol Diuretics
Isosorbide, furosemide, hydrochlorothiazide, spironolactone, triamterene and naftopidil Antihypertensives
Delapril hydrochloride, captopril, perindopril erbumine, hydralazine hydrochloride, labetalol hydrochloride, nicardipine hydrochloride, nilvadipine, nifedipine, diltiazem, nitrendipine, barnidipine hydrochloride, efonidipine hydrochloride, amlodipine besilate, felodipine, cilnidipine, aranidipine, manidipine hydrochloride, losartan potassium and candesartan cilexetil Vasoconstrictors
Phenylephrine hydrochloride, pseudoephedrine and phenylpropanolamine hydrochloride Vasodilators
Verapamil hydrochloride and cinnarizine Hypolipidemic Drugs
Cerivastatin sodium, simvastatin, pravastatin sodium, atorvastatin calcium hydrate and clofibrate Respiratory Stimulants
Levallorphan tartrate Antitussives
  Cloperastine and dextromethorphan hydrobromide
Expectorants
  Ambroxol hydrochloride, bromhexine hydrochloride and L-carbocysteine
Antitussive and Expectorant Drugs
  Potassium guaiacolsulfonate, guaifenesin, codeine phosphate, dihydrocodeine phosphate, methylephedrine hydrochloride, tipepidine hibenzate, trimetoquinol hydrochloride and dextromethorphan phenolphthalinate
Bronchodilators
  Theophylline, salbutamol sulfate, orciprenaline sulfate, methoxyphenamine hydrochloride, trimetoquinol, procaterol and montelukast sodium
Gargles
  Azulene and povidone-iodine
Antidiarrheals and Intestinal Regulators
  Loperamide hydrochloride, berberine, lactomin, spore forming lactic acid bacteria, bifidobacteria, *Bacillus subtilis* var. *natto* and *Clostridium butyricum*
Antiulcer Drugs
  Lansoprazole, omeprazole, rabeprazole, famotidine, cimetidine, ranitidine hydrochloride, sulpiride, deprenone and sucralfate
Stomachics
  Diastase, Scopolia extract, cellulase AP3, lipase AP and cinnamon oil
Antacids
  Magnesium carbonate, sodium bicarbonate, magnesium aluminometasilicate, synthetic hydrotalcite, precipitated calcium carbonate and magnesium oxide
Laxatives
  Sennoside, calcium sennoside, bisacodyl and sodium picosulfate
Cholagogues
  Dehydrocholic acid and trepibutone
Analeptics
  Vitamins such as vitamin A, vitamin D, vitamin E (d-α-tocopherol acetate and the like), vitamin B1 (dibenzoyl thiamine, fursultiamine hydrochloride, and the like), vitamin B2 (riboflavin butyrate and the like), vitamin B6 (pyridoxine hydrochloride and the like), vitamin C (ascorbic acid, sodium L-ascorbate, and the like) and vitamin B12 (hydroxocobalamin acetate, mecobalamin, cyanocobalamin, and the like); minerals such as calcium, magnesium and iron; proteins, amino acids and crude drugs
Antipodagrics
  Allopurinol and colchicine
Anti-diabetic Drugs
  Tolbutamide, glibenclamide, acarbose, voglibose and pioglitazone hydrochloride
Antibiotics
  Cephalexin, cefaclor, amoxicillin, pipmecillinam hydrochloride, cefotiam hexetil hydrochloride, cefadroxil, cefixime, cefditoren pivoxil, cefteram pivoxil, cefpodoxime proxetil, ampicillin, ciclacillin, enoxacin and carumonam sodium
Antimicrobials
  Triclosan, cetylpyridinium chloride, domiphen bromide, quaternary ammonium salts, zinc compounds, sanguinarine, fluorides, alexidine, octenidine, EDTA, nalidixic acid, enoxacin, ofloxacin, sulfamethoxazole and trimethoprim
Osteoporosis Drugs
  Ipriflavone and alendronate sodium
Skeletal Muscle Relaxants
  Methocarbamol
Antirheumatic Agents
  Methotrexate and bucillamine
Hormonal Drugs
  Liothyronine sodium, dexamethasone sodium phosphate, prednisolone, oxendolone, leuprorelin acetate, triamcinolone acetonide and hydrocortisone
Alkaloidal Narcotics
  Opium, morphine hydrochloride, ipecac, oxycodone hydrochloride, opium alkaloids hydrochlorides and cocaine hydrochloride
Blood Coagulation Inhibitor
  Dicumarol
Antineoplastics
  5-fluorouracil, uracil, mitomycin, manidipine hydrochloride and pioglitazone hydrochloride
Parasympatholytics
  Belladonna total alkaloid, Datura extract, homatropine, tropicamide, butylscopolamine and mepenzolate
Antihistaminics and Antiallergics
  Chlorpheniramine maleate, carbinoxamine maleate, clemastine fumarate, diphenhydramine hydrochloride, diphenhydramine citrate, diphenylpyraline hydrochloride, promethazine hydrochloride, triprolidine hydrochloride, loratadine, mequitazine, amlexanox, seratrodast, sodium cromoglycate, ketotifen fumarate, pranlukast hydrate, fexofenadine hydrochloride, bepotastine besilate, cetirizine hydrochloride and epinastine hydrochloride
Others
  Nicotine and nicotine resinate The food component used as the active ingredient is not particularly limited as long as the intake with the film preparation is possible. The food component may be in any state of solid or liquid at normal temperature. Specific examples of the food component include flavors, juices, plant extracts, animal extracts, vitamins, and the like.

More specific examples thereof include menthol, a lemon oil, peppermint, spearmint, a juice from *Perilla frutescens*, coenzyme Q10, *Aloe arborescens* extract, *Silybum perforatum* extract, *Silybum marianum* extract, *Ginkgo biloba* leaf extract, *Vitis vinifera* leaf extract, *Serenoa repens* fruit extract, pumpkin seed extract, *Vitex agnus castus* extract, *Valeriana officinalis* extract, hop extract, rose hip extract, echinacea extract, ginger extract, garlic extract, DHA, EPA, lactoferrin extract, vitamins, amino acids, sardine peptide, and the like.

Here, some of the above-described substances belong to both of the drug and the food component due to their own natures. In this case, the film including such a substance can be used for a drug or a food component based on the purpose to be used.

The active ingredient used in the present invention is a known compound, and is easily available in the market or can be synthesized.

In addition, the active ingredient can be used singly or in combination of two or more kinds.

The active ingredient may provide the film preparation with bitter taste and/or unpleasant taste depending on the type or the amount to be added. When the film preparation is for oral administration, it is preferable that barrier at the time of dosage be removed by masking the bitter taste and/or unpleasant taste.

Examples of the active ingredient providing bitter taste and/or unpleasant taste include fexofenadine hydrochloride, cetirizine hydrochloride, mequitazine, diphenhydramine hydrochloride, dextromethorphan hydrobromide, fluvoxamine maleate, phenylephrine hydrochloride, and the like.

Masking method applicable in the present invention is not particularly limited. However, a method using a masking reagent is preferable from the viewpoint of taking advantage of the film preparation which is taken by being dissolved in the oral cavity. Specific examples of such a method include inclusion by a cyclodextrin, adsorption by an ion-exchange resin, and microencapsulation (or micromatrix formation) by using a substance having a poor solubility to water.

As the cyclodextrin which serves as the masking reagent, alpha type, beta type and gamma type cyclodextrins can be used. The type of the cyclodextrin can be adequately selected based on the physical and chemical properties (molecular weight and the like) of the active ingredient. The inclusion by the cyclodextrin may be performed in advance before preparation of the active-ingredient-containing layer. Alternatively, the inclusion by the cyclodextrin may be performed by simultaneously mixing other components (the active ingredient, the water soluble polymer and the disintegrating agent) therewith at the time of preparation of the active-ingredient-containing layer.

As the ion-exchange resin which serves as the masking reagent, a cation-exchange resin and an anion-exchange resin can be used. Specific examples thereof include AMBERLITE IRP69, IRP64, IRP88 and IRP43 manufactured by ROHM AND HAAS FRANCE S.A.S. The type of the ion-exchange resin can be adequately selected based on the physical and chemical properties (pH and the like) of the active ingredient. The adsorption by the ion-exchange resin may be performed in advance before preparation of the active-ingredient-containing layer. Alternatively, the adsorption by the ion-exchange resin may be performed by simultaneously mixing other components (the active ingredient, the water soluble polymer and the disintegrating agent) therewith at the time of preparation of the active-ingredient-containing layer.

Examples of the substance having a poor solubility to water, which serves as the masking reagent, include the above-described ion-exchange resin, stearic acid, stearyl alcohols, hydrogenated oils, waxes (for example, carnauba wax), ethyl cellulose, acrylic polymers, polylactic acid, hydroxypropyl methyl cellulose phthalate, polyvinyl acetal diethylaminoacetate, carboxy methyl ethyl cellulose, and the like. The type of the substance having a poor solubility to water can be adequately selected based on the physical and chemical properties (the intensity of bitter taste, solubility, pH, melting point, and the like) of the active ingredient.

It is preferable that the microencapsulation (micromatrix formation) by using the substance having a poor solubility to water be performed in advance before preparation of the active-ingredient-containing layer. Specifically, a microcapsule or a micromatrix is formed by covering the active ingredient with the substance having a poor solubility to water or mixing the active ingredient into the substance having a poor solubility to water by kneading. A preferable forming method is a spray cooling method. The particle diameter (average particle diameter determined by a laser diffraction/scattering method) of the microcapsule and micromatrix is preferably from 10 to 300 μm from the viewpoint that the film preparation does not provide sandy feeling when dissolved in the oral cavity.

The content of the active ingredient in the film preparation of the present invention (based on the dried product, hereinafter the same) varies depending on the type of the used components, and the like. However, the content is generally from 0.1 to 75.0% by mass, preferably from 0.1 to 60.0% by mass, and particularly preferably from 0.1 to 50.0% by mass relative to the total mass of the film preparation.

The water soluble polymer constituting the active-ingredient-containing layer is a substance selected from the group consisting of methyl cellulose, hydroxypropyl cellulose and hydroxypropyl methyl cellulose. Methyl cellulose, hydroxypropyl cellulose and hydroxypropyl methyl cellulose are not particularly limited as long as they are acceptable as a formulation and can form a film.

The content of methoxyl group in methyl cellulose (based on the dried product) is from 10.0 to 50.0%, preferably from 20.0 to 40.0%, and particularly preferably 26.0 to 33.0%, based on values measured by a gas chromatograph method. The film formability is excellent, when the content of methoxyl group is in the range from 10.0 to 50.0%.

The kinematic viscosity of methyl cellulose refers to a kinematic viscosity in a 2%-aqueous solution form thereof at 20° C., and is from 4 to 100000 mPa·s, preferably from 5 to 10000 mPa·s, and particularly preferably from 10 to 500 mPa·s by measurement in accordance with Method I of Viscosity Determination in Japanese Pharmacopoeia. The workability in the film formation and the dissolution of the obtained film in the oral cavity are excellent, when the kinematic viscosity is in the range from 4 to 100000 mPa·s.

Specific examples of methyl cellulose having the above-descried properties include one available from Shin-Et su Chemical Co., Ltd. as the product name: Metolose SM-25 (methoxyl group content of 26.0 to 33.0%, kinematic viscosity of 25 mPa·s), and the like.

Methyl cellulose described above is a known compound, and is easily available in the market or can be synthesized.

The content of hydroxypropoxyl group in hydroxypropyl cellulose (based on the dried product) is from 30.0 to 90.0%, preferably from 40.0 to 85.0%, and particularly preferably 50.0 to 80.0%, based on values measured by a gas chromatograph method. The film formability is excellent, when the content of hydroxypropoxyl group is in the range from 30.0 to 90.0%.

The kinematic viscosity of hydroxypropyl cellulose refers to a kinematic viscosity in a 2%-aqueous solution form thereof at 20° C., and is from 0.5 to 4000 mPa·s, preferably from 1 to 400 mPa·s, and particularly preferably from 2.0 to 10 mPa·s by measurement in accordance with Method I of Viscosity Determination in Japanese Pharmacopoeia. The workability in the film formation and the dissolution of the obtained film in the oral cavity are excellent, when the kinematic viscosity is in the range from 0.5 to 4000 mPa·s.

Specific examples of hydroxypropyl cellulose having the above-descried properties include one available from Nippon Soda Co., Ltd. as the product name: HPC-SSL (hydroxypropoxyl group content of 53.4 to 77.5%, kinematic viscosity of 2.0 to 2.9 mPa·s), and the like.

Hydroxypropyl cellulose described above is a known compound, and is easily available in the market or can be synthesized.

The contents of methoxyl group and hydroxypropoxyl group in hydroxypropyl methyl cellulose (based on the dried product) are from 5.0 to 50.0% in the case of methoxyl group and from 2.0 to 20.0% in the case of hydroxypropoxyl group, preferably from 15.0 to 40.0% in the case of methoxyl group and from 5.0 to 15.0% in the case of hydroxypropoxyl group, and particularly preferably from 28.0 to 30.0% in the case of methoxyl group and from 7.0 to 12.0% in the case of hydroxypropoxyl group, based on values measured by a gas chromatograph method. The film formability is excellent, when the contents of methoxyl group and hydroxypropoxyl group are in the ranges from 5.0 to 50.0% and from 2.0 to 20.0%, respectively.

The kinematic viscosity of hydroxypropyl methyl cellulose refers to a kinematic viscosity in a 2%-aqueous solution form thereof at 20° C., and is from 0.1 to 20.0 mPa·s, preferably from 1.0 to 15.0 mPa·s, and particularly preferably from 2.0 to 5.0 mPa·s by measurement in accordance with Method I of Viscosity Determination in Japanese Pharmacopoeia. The workability in the film formation and the dissolution of the obtained film in the oral cavity are excellent, when the kinematic viscosity is in the range from 0.1 to 20.0 mPa·s.

Specific examples of hydroxypropyl methyl cellulose having the above-descried properties include one available from Shin-Etsu Chemical Co., Ltd. as the product name: H.P.M.C TC-5E (methoxyl group content of 28.0 to 30.0%, hydroxypropoxyl group content of 7.0 to 12.0%, kinematic viscosity of 2.5 to 3.5 mPa·s), and the like.

Hydroxypropyl methyl cellulose described above is a known compound, and is easily available in the market or can be synthesized.

Methyl cellulose, hydroxypropyl cellulose and hydroxypropyl methyl cellulose can be used singly or in combination.

When methyl cellulose and hydroxypropyl cellulose are used in combination, the compounding ratio of methyl cellulose and hydroxypropyl cellulose is from 20:80 to 80:20, preferably from 30:70 to 60:40, and particularly preferably from 40:60 to 50:50 on the mass basis.

When methyl cellulose and hydroxypropyl methyl cellulose are used in combination, the compounding ratio of methyl cellulose and hydroxypropyl methyl cellulose is from 20:80 to 80:20, preferably from 30:70 to 60:40, and particularly preferably from 40:60 to 50:50 on the mass basis.

When hydroxypropyl cellulose and hydroxypropyl methyl cellulose are used in combination, the compounding ratio of hydroxypropyl cellulose and hydroxypropyl methyl cellulose is from 30:70 to 70:30, preferably from 60:40 to 40:60, and particularly preferably from 60:40 to 50:50 on the mass basis.

When methyl cellulose, hydroxypropyl cellulose and hydroxypropyl methyl cellulose are used in combination, the compounding ratio of methyl cellulose, hydroxypropyl cellulose and hydroxypropyl methyl cellulose is from 15:60:25 to 55:15:30, preferably from 15:35:50 to 45:30:25, and particularly preferably from 20:30:50 to 35:30:35 on the mass basis.

The content of the water soluble polymer in the film preparation of the present invention (based on the dried product, hereinafter the same) (when multiple bases are used in combination, the content is based on the total content thereof) is from 1.0 to 40.0% by mass, preferably from 5.0 to 35.0% by mass, and particularly preferably from 10.0 to 30.0% by mass relative to the total mass of the film preparation. The film formability is particularly excellent, when the content is in the range from 1.0 to 40.0% by mass.

When a water-foamable disintegrating agent is used as the disintegrating agent, which will be described below, hydroxypropyl cellulose is preferably used as the water soluble polymer. This is because of the following reason. Specifically, at the time of preparation of a active-ingredient-containing layer, a low-water-content solvent (for example, an aqueous solution of high ethanol concentration) is preferably used as the solvent for preparing the active-ingredient-containing layer in order to suppress foaming (decomposition) of the water-foamable disintegrating agent, the foaming (decomposition) being due to the contacting with water. On the other hand, hydroxypropyl cellulose can be dissolved in ethanol, and demonstrates an excellent film formability.

The disintegrating agent refers to a substance capable of disintegrating the active-ingredient-containing layer to release the drug or the food component included in the layer, when the film preparation of the present invention is taken. The disintegrating agent is roughly classified into a water-foamable disintegrating agent and a water-non-foamable disintegrating agent.

The water-foamable disintegrating agent refers to a substance which demonstrates a disintegration effect by generating gas upon contact with water. The water-foamable disintegrating agent can further be classified into an acidifying agent (which reacts with an alkali under the presence of water to generate gas), an alkalizing agent (which reacts with an acid under the presence of water to generate gas) and an alkaline water-foamable disintegrating agent. Examples of the acidifying agent include tartaric acid, citric acid, maleic acid, fumaric acid, malic acid, adipic acid, succinic acid, lactic acid, glycolic acid, α-hydroxy acids, ascorbic acid, amino acids, and salts and derivatives of these acids. Examples of the alkalizing agent include potassium carbonate, lithium carbonate, sodium carbonate, calcium carbonate, ammonium carbonate, L-lysine carbonate, arginine carbonate, glycine sodium carbonate, sodium carbonates of amino acids, anhydrous sodium perborate, effervescent perborate salts, sodium perborate monohydrate, sodium bicarbonate, sodium percarbonate, sodium dichloroisocyanurate, sodium hypochlorite, calcium hypochlorite, and the like.

The type of the water-foamable disintegrating agent can be adequately selected based on the physical and chemical properties (pH, particle diameter, and the like) of the active ingredient.

The water-foamable disintegrating agent is preferably used when the content of the active ingredient in the film preparation is high (for example, from 5.0 to 40.0% by mass relative to the total mass of the film preparation). This is because the active ingredient can be more rapidly released during the dosage.

The water-foamable disintegrating agent can be used singly or in combination of two or more kinds.

A specific example of the water-foamable disintegrating agent includes one available from Iwata Chemical Co., Ltd. as the product name: citric acid.

The water-foamable disintegrating agent described above is a known compound, and is easily available in the market or can be synthesized.

The water-non-foamable disintegrating agent refers to a substance which demonstrates a disintegration effect without generating gas upon contact with water (for example, demonstrates a disintegration effect by swelling upon absorbing water). Examples of the water-non-foamable disintegrating agent include crystalline cellulose, carboxymethyl cellulose sodium, carboxymethyl cellulose, carmellose sodium, croscarmellose sodium, carboxymethyl cellulose calcium, starches, dextrin, hydroxy propyl starch, carboxymethyl starch sodium, low substituted hydroxypropyl cellulose (hydroxypropyl cellulose having a hydroxypropoxyl group content of 16% or less (based on the dried product) based on values measured by a gas chromatograph method), and a mixture of crystalline cellulose and carboxymethyl cellulose sodium.

The particle diameter (average particle diameter determined by a laser diffraction/scattering method) of the water-non-foamable disintegrating agent is preferably from 1 to 1000 μm from the viewpoint of suspension stability.

The type of the water-non-foamable disintegrating agent can be adequately selected based on the physical and chemical properties (pH, particle diameter, and the like) of the active ingredient.

The water-non-foamable disintegrating agent can be used singly or in combination of two or more kinds.

The mixture of crystalline cellulose and carboxymethyl cellulose sodium is preferable as the water-non-foamable disintegrating agent.

Furthermore, the mixture of crystalline cellulose and carboxymethyl cellulose sodium is preferably a colloidal grade from the viewpoint of stabilizing suspension of the solid content in a film forming solution during the preparation of the active-ingredient-containing layer. The colloidal grade refers to a mixture in which the compounding ratio of crystalline cellulose and carboxymethyl cellulose sodium (based on the dried mass) (crystalline cellulose:carboxymethyl cellulose sodium) is from 91.7:8.3 to 80.0:20.0. A specific example includes one available from Asahi Kasei Chemicals Corporation as the product name: Ceolus RC-A591NF (a mixture of crystalline cellulose and carboxymethyl cellulose sodium, compounding ratio (mass basis) of 80:20, kinematic viscosity of 30 to 100 mPa·s, average particle diameter of 50 μm determined by a laser diffraction/scattering method).

The water-non-foamable disintegrating agent described above is a known compound, and is easily available in the market or can be synthesized.

A plasticizer, an emulsifier, a sweetener, a corrective, an aromatizer, and the like can be added to the active-ingredient-containing layer, if necessary. Specifically, examples thereof include the following substances.

Plasticizers

Triethyl citrate, glycerin, sorbitol, triacetin, propylene glycol, polyoxyethylene (105) polyoxypropylene (5) glycol, polysorbate, macrogol, glyceryl monostearate and mannitol Emulsifiers Alkylbenzene sulfonate, carrageenan, carboxy vinyl polymers, guar gum, glycerin fatty acid esters, sucrose fatty acid esters, stearic acid, lanolin, egg-yolk lecithin, cetanol, sorbitan fatty acid esters, soybean lecithin, sorbitan trioleate, pectin, polyoxyethylene hydrogenated castor oil, sodium lauryl sulfate and lauromacrogol Sweeteners Acesulfame potassium, aspartame, dipotassium glycyrrhizinate, saccharin, sodium saccharin, thaumatin and stevia Correctives Adipic acid, ascorbic acid, citric acid, tartaric acid, tannic acid, fumaric acid, malic acid, methyl salicylate and L-menthol Aromatizers Fennel oil, orange oil, chamomile oil, camphor, cinnamon oil, salvia oil, spearmint oil, clove oil, mentha oil, vanillin, peppermint extract, bergamot oil, borneol, eucalyptus oil, lavender oil, lemon oil, rose oil and Roman chamomile oil In the active-ingredient-containing layer, the total content of the active ingredient and the water soluble polymer (based on the dried product, hereinafter the same) is from 15.0% by mass to 95.0% by mass, preferably from 20.0% by mass to 90.0% by mass, and particularly preferably from 30.0% by mass to 80.0% by mass of the total mass of the active-ingredient-containing layer. The film formability and the rapid solubility are excellent, when the total content of the active ingredient and the water soluble polymer is in the range from 15.0 by mass to 95.0% by mass of the total mass of the active-ingredient-containing layer.

The active-ingredient-free layer comprises methyl cellulose and/or hydroxypropyl methyl cellulose. More specifically, the active-ingredient-free layer comprises methyl cellulose singly, hydroxypropyl methyl cellulose singly, or methyl cellulose and hydroxypropyl methyl cellulose in combination.

Methyl cellulose and hydroxypropyl methyl cellulose constituting the active-ingredient-free layer can provide flexibility to the film preparation made of the combination of the active-ingredient-free layer and the active-ingredient-containing layer when formed into a film.

The active-ingredient-free layer does not include the above-described active ingredient.

The content of methoxyl group in methyl cellulose constituting the active-ingredient-free layer (based on the dried product) is from 10 to 50%, preferably from 20 to 40%, and particularly preferably from 25 to 35%, based on values measured by a gas chromatograph method. The film formability is excellent, when the content of methoxyl group is in the range from 10 to 50%.

The kinematic viscosity of methyl cellulose refers to a kinematic viscosity in a 2%-aqueous solution form thereof at 20° C., and is from 4 to 100000 mPa·s, preferably from 4 to 10000 mPa·s, and particularly preferably from 4 to 500 mPa·s by measurement in accordance with Method I of Viscosity Determination in Japanese Pharmacopoeia. The workability in the film formation and the dissolution of the obtained film in the oral cavity are excellent, when the kinematic viscosity is in the range from 4 to 100000 mPa·s.

Specific examples of methyl cellulose having the above-descried properties include one available from Shin-Etsu Chemical Co., Ltd. as the product name: Metolose SM-25 (methoxyl group content of 26.0 to 33.0%, kinematic viscosity of 25 mPa·s), and the like.

Methyl cellulose described above is a known compound, and is easily available in the market or can be synthesized.

The contents of methoxyl group and hydroxypropoxyl group in hydroxypropyl methyl cellulose constituting the active-ingredient-free layer (based on the dried product) are from 5 to 50% in the case of methoxyl group and from 2 to 20% in the case of hydroxypropoxyl group, preferably from 15 to 40% in the case of methoxyl group and from 5 to 15% in the case of hydroxypropoxyl group, and particularly preferably from 28 to 30% in the case of methoxyl group and from 7 to 12% in the case of hydroxypropoxyl group, based on values measured by a gas chromatograph method. The film formability is excellent, when the contents of methoxyl group and hydroxypropoxyl group are in the ranges from 5 to 50% and from 2 to 20%, respectively.

The kinematic viscosity of hydroxypropyl methyl cellulose refers to a kinematic viscosity in a 2%-aqueous solution form thereof at 20° C., and is from 1 to 50 mPa·s, preferably from 10 to 20 mPa·s, and particularly preferably from 12.5 to 17.5 mPa·s by measurement in accordance with Method I of Viscosity Determination in Japanese Pharmacopoeia. The workability in the film formation and the dissolution of the obtained film in the oral cavity are excellent, when the kinematic viscosity is in the range from 1 to 20 mPa·s.

Specific examples of hydroxypropyl methyl cellulose having the above-descried properties include one available from Shin-Etsu Chemical Co., Ltd. as the product name: TC-5S (methoxyl group content of 28 to 30%, hydroxypropoxyl group content of 7 to 12%, kinematic viscosity of 12.5 to 17.5 mPa·s), and the like.

Hydroxypropyl methyl cellulose described above is a known compound, and is easily available in the market or can be synthesized.

When methyl cellulose and hydroxypropyl methyl cellulose are used in combination, the compounding ratio of methyl cellulose and hydroxypropyl methyl cellulose is from 20:80 to 80:20, preferably from 30:70 to 60:40, and particularly preferably from 40:60 to 50:50 on the mass basis.

A plasticizer, a disintegrating agent, a corrective, aromatizer, a colorant, and the like can be added to the active-ingredient-free layer, if necessary.

Preferably, the active-ingredient-free layer does not include these additives. In this case, the active-ingredient-free layer consists of methyl cellulose and/or hydroxypropyl methyl cellulose.

The film preparation of the present invention can be prepared by common methods for preparing a multilayer film preparation.

For example, a film preparation can be formed by separately preparing an active-ingredient-containing layer and an active-ingredient-free layer and pasting the two layers on each other.

As another method, a film preparation can also be formed by initially forming an active-ingredient-free layer and directly forming an active-ingredient-containing layer thereon.

The active-ingredient-containing layer can be prepared, for example, by the following method including the steps of;

(1) forming a solution or a dispersion by dissolving or dispersing an active ingredient, a water soluble polymer, a disintegrating agent and any additive in a solvent; and (2) spreading the obtained solution or dispersion onto a framework for film formation, removing the solvent therefrom to thereby form a film, releasing the formed film from the framework, and cutting the film into a predetermined size.

In step (1), water, ethanol, a mixture thereof, or the like can be used as the solvent.

Here, when a water-foamable disintegrating agent is used as the disintegrating agent, an aqueous solution of high ethanol concentration is preferably used as the solvent. The use of the aqueous solution of high ethanol concentration can suppress decomposition of the disintegrating agent by water. The concentration of ethanol in the aqueous solution of high ethanol concentration is from 70 to 100% by volume, preferably from 75 to 100% by volume, and particularly preferably from 80 to 100% by volume.

Note that methyl cellulose can be dissolved into an ethanol solution of 60% by volume or less. Hydroxypropyl methyl cellulose can be dissolved into an ethanol solution of 80% by volume or less. Hydroxypropyl cellulose can be dissolved into an ethanol solution of 100% by volume.

In step (2), polyethylene terephthalate, polypropylene, or the like can be used as the material of the framework for film formation. Among these, polyethylene terephthalate is preferable from the viewpoint of releasability of the obtained film. The solvent can be dried at 30 to 90° C., and preferably at 40 to 70° C. A preferable drying method is through circulation drying method from the viewpoint that the film loss is small.

The active-ingredient-free layer can be prepared, for example, by the following method including the steps of;

(1) forming a solution or a dispersion by dissolving or dispersing methyl cellulose and/or hydroxypropyl methyl cellulose and any additive in a solvent; and (2) spreading the obtained solution or dispersion onto a framework for film formation, removing the solvent therefrom to thereby form a film, releasing the formed film from the framework, and cutting the film into a predetermined size.

In step (1), water, ethanol, a mixture thereof, or the like can be used as the solvent. Among these, water is preferable from the viewpoint of influence on human body and the environment.

In step (2), polyethylene terephthalate, polypropylene, or the like can be used as the material of the framework for film formation. Among these, polyethylene terephthalate is preferable from the viewpoint of releasability of the obtained film. The solvent can be dried at 30 to 90° C., and preferably at 40 to 70° C. A preferable drying method is through circulation drying method from the viewpoint that the film loss is small.

The film preparation of the present invention may have a two-layer structure formed of one active-ingredient-containing layer and one active-ingredient-free layer, or may have a three-layer structure formed by disposing two active-ingredient-free layers on both sides of one active-ingredient-containing layer.

The thickness (sum of the thickness of the active-ingredient-containing layer and the thickness of the active-ingredient-free layer) of the film preparation of the present invention varies depending on the type of a target to be applied, and the like. However, when the film preparation is administered in the oral cavity, the thickness thereof is from 0.005 to 2.000 mm, preferably from 0.010 to 1.000 mm, and particularly preferably from 0.020 to 0.500 mm. When the thickness is from 0.005 to 2.000 mm, foreign-body sensation during dosage can be suppressed.

In the film preparation of the present invention, the thickness of the active-ingredient-containing layer is from 0.001 to 2.000 mm, preferably from 0.010 to 1.000 mm, and particularly preferably from 0.020 to 0.500 mm. When the thickness is from 0.001 to 2.000 mm, foreign-body sensation during dosage can be suppressed and the flexibility can be maintained.

In the film preparation of the present invention, the thickness of the active-ingredient-free layer (when a number of the active-ingredient-free layers exist, a sum of the thicknesses thereof is used) is from 0.0001 to 0.1000 mm, preferably from 0.0010 to 0.0500 mm, and particularly preferably from 0.0020 to 0.0200 mm. When the thickness is from 0.0001 to 0.1000 mm, foreign-body sensation during dosage can be suppressed and the flexibility can be maintained.

The film preparation of the present invention has a rapid solubility. The rapid solubility means that a dissolution time is within 40 seconds, which is measured in accordance with a second method (Paddle Method) of Dissolution Test in Japanese Pharmacopoeia (testing conditions: the number of rotations: 50 rpm, temperature: 37±0.5° C., testing liquid: purified water, quantity of testing liquid: 900 ml). Preferably, the film preparation of the present invention has a dissolution time within 30 seconds.

The shape of the film preparation of the present invention varies depending on the type of a target to be applied, and the like. For example, the shape is a rectangular shape, circular shape, elliptic shape, or the like. The shape is preferably circular or elliptic from the viewpoint of suppressing foreign-body sensation during intake.

The size of the film preparation of the present invention varies depending on the type of a target to be applied, and the like. However, when the film preparation is administered as a rectangular film in the oral cavity, the length of the minor axis is from 5 to 30 mm, preferably from 8 to 25 mm, and particularly preferably from 10 to 25 mm, while the length of the major axis is from 10 to 40 mm, preferably from 15 to 40 mm, and particularly preferably from 20 to 35 mm.

The film preparation of the present invention is generally administered in the oral cavity. However, the film preparation can be administered in sites other than the oral cavity, for example, intestinal mucous membrane, conjunctival sac, nose, throat, vagina, and the like.

In addition, the film preparation of the present invention can be used targeting any of systemic action and local action, depending on the properties of the included active ingredient.

Note that, since having a rapid solubility, the film preparation of the present invention is used differently from a sustained release-type film preparation which releases an active ingredient upon attachment to an affected part.

The present invention is not limited to a particular theory. However, it is considered that the reasons why the film preparation of the present invention has both rapid solubility and flexibility at the same time are because: the rapid solubility of the film is ensured by the water soluble polymer and the disintegrating agent in the active-ingredient-containing layer; and the flexibility of the film is ensured by the active-ingredient-free layer.

Hereinafter, the effects of the present invention will be specifically described with reference to Examples, but the present invention is not limited to Examples.

EXAMPLES

Example 1-A

Two-layer Film Preparation Including Crystalline Cellulose as Disintegrating Agent A film preparation having a two-layer structure formed of one active-ingredient-containing layer and one active-ingredient-free layer was prepared.
(1) Preparation of Active-ingredient-free Layer A solution was prepared by dissolving 10.0 g of hydroxypropyl methyl cellulose (methoxyl group content of 28 to 30%, hydroxypropoxyl group content of 7 to 12%, kinematic viscosity of 12.5 to 17.5 mm$^2$/s) (manufactured by Shin-Etsu Chemical Co., Ltd., product name: TC-5S) as a water soluble polymer and 1.0 g of concentrated glycerin as a plasticizer into 90 ml of purified water as a solvent.

The obtained solution was spread onto a polyethylene terephthalate-made framework for film formation by using a baker applicator (manufactured by Imoto Machinery Co., Ltd.). Through-circulation drying was performed on the solvent under 60° C. to remove the solvent. Thus, a film was formed.
(2) Preparation of Active-ingredient-containing Layer A solution was prepared by dissolving 6.0 g of d-chlorpheniramine maleate and 0.6 g of belladonna alkaloid as active ingredients, 30.0 g of hydroxypropyl methyl cellulose (methoxyl group content of 28.0 to 30.0%, hydroxypropoxyl group content of 7.0 to 12.0%, kinematic viscosity of 2.5 to 3.5 mm$^2$/s) (manufactured by Shin-Etsu Chemical Co., Ltd., product name: H.P.M.C TC-5E) as a water soluble polymer, 12.0 g of a sucrose fatty acid ester as an emulsifier, 3.0 g of acesulfame potassium and 3.0 g of aspartame as sweeteners, 6.6 g of L-menthol as a corrective, 18.0 g of concentrated glycerin as a plasticizer and 56.7 g of a mixture of crystalline cellulose and carboxymethyl cellulose sodium (compounding ratio (mass basis) of 80:20, kinematic viscosity of 30 to 100 mPa·s) (manufactured by Asahi Kasei Chemicals Corporation, product name: Ceolus RC-A591NF) as a water-non-foamable disintegrating agent into 120.0 g of an aqueous solution of high ethanol concentration (ethanol concentration: 80% by volume) as a solvent.

The obtained solution was spread onto the framework on which the active-ingredient-free layer was formed by using the baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.14 mm (the active-ingredient-containing layer: 0.13 mm, the active-ingredient-free layer: 0.01 mm). The content of the active ingredients (based on the dried product, defined as the same in following Examples and Comparative Examples) was 4.5% by mass relative to the total mass of the film preparation. The content of the water soluble polymer (based on the dried product, defined as the same in following Examples and Comparative Examples) was 27.2% by mass relative to the total mass of the film preparation. In addition, the total content of the active ingredients and the water soluble polymer in the obtained active-ingredient-containing layer (based on the dried product, defined as the same in following Examples and Comparative Examples) was 31.7% by mass relative to the total mass of the active-ingredient-containing layer.

Comparative Example 1-B

Two-layer Film Preparation not Including Disintegrating Agent

A film preparation having a two-layer structure formed of one active-ingredient-containing layer not including a disintegrating agent and one active-ingredient-free layer was prepared.
(1) Preparation of Active-ingredient-free Layer A solution was prepared by dissolving 10.0 g of hydroxypropyl methyl cellulose (methoxyl group content of 28 to 30%, hydroxypropoxyl group content of 7 to 12%, kinematic viscosity of 12.5 to 17.5 mm$^2$/s) (manufactured by Shin-Etsu Chemical Co., Ltd., product name: TC-5S) as a water soluble polymer and 1.0 g of concentrated glycerin as a plasticizer into 90 ml of purified water as a solvent.

The obtained solution was spread onto a polyethylene terephthalate-made framework for film formation by using a baker applicator (manufactured by Imoto Machinery Co., Ltd.). Through-circulation drying was performed on the solvent under 60° C. to remove the solvent. Thus, a film was formed.
(2) Preparation of Active-ingredient-containing Layer A solution was prepared by dissolving 6.0 g of d-chlorpheniramine maleate and 0.6 g of belladonna alkaloid as active ingredients, 30.0 g of hydroxypropyl methyl cellulose (methoxyl group content of 28.0 to 30.0%, hydroxypropoxyl group content of 7.0 to 12.0%, kinematic viscosity of 2.5 to 3.5 mm$^2$/s) (manufactured by Shin-Etsu Chemical Co., Ltd., product name: H.P.M.C TC-5E) as a water soluble polymer, 12.0 g of a sucrose fatty acid ester as an emulsifier, 3.0 g of acesulfame potassium and 3.0 g of aspartame as sweeteners, 6.6 g of L-menthol as a corrective and 18.0 g of concentrated glycerin as a plasticizer into 120.0 g of an aqueous solution of high ethanol concentration (ethanol concentration: 80% by volume) as a solvent.

The obtained solution was spread onto the framework on which the active-ingredient-free layer was formed by using the baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.14 mm (the active-ingredient-containing layer: 0.13 mm, the active-ingredient-free layer: 0.01 mm). The content of the active ingredients was 7.3% by mass relative to the total mass of the film preparation. The content of the water soluble polymer was 44.3% by mass relative to the total mass of the film preparation. In addition, the total content of the active ingredients and the water soluble polymer in the obtained active-ingredient-containing layer was 51.7% by mass relative to the total mass of the active-ingredient-containing layer.

Comparative Example 1-C

Monolayer Film Preparation not Including Disintegrating Agent

A film preparation having a monolayer structure formed of only an active-ingredient-containing layer not including a disintegrating agent was prepared.
(1) Preparation of Active-Ingredient-Containing Layer A solution was prepared by dissolving 6.0 g of d-chlorpheniramine maleate and 0.6 g of belladonna alkaloid as active ingredients, 30.0 g of hydroxypropyl methyl cellulose (methoxyl group content of 28.0 to 30.0%, hydroxypropoxyl group content of 7.0 to 12.0%, kinematic viscosity of 2.5 to 3.5 mm$^2$/s) (manufactured by Shin-Etsu Chemical Co., Ltd., product name: H.P.M.C TC-5E) as a water soluble polymer, 12.0 g of a sucrose fatty acid ester as an emulsifier, 3.0 g of acesulfame potassium and 3.0 g of aspartame as sweeteners, 6.6 g of L-menthol as a corrective and 18.0 g of concentrated glycerin as a plasticizer into 120.0 g of an aqueous solution of high ethanol concentration (ethanol concentration: 80% by volume) as a solvent.

The obtained solution was spread onto a framework for film formation by using a baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.14 mm. The content of the active ingredients was 8.3% by mass relative to the total mass of the film preparation. The content of the water soluble polymer was 37.9% by mass relative to the total mass of the film preparation. In addition, the total content of the active ingredients and the water soluble polymer in the obtained active-ingredient-containing layer was 46.2% by mass relative to the total mass of the active-ingredient-containing layer.

Comparative Example 1-D

Three-layer Film Preparation not Including Disintegrating Agent

A film preparation having a three-layer structure formed of one active-ingredient-containing layer not including a disintegrating agent and two active-ingredient-free layers was prepared.
(1) Preparation of First Active-ingredient-free Layer A solution was prepared by dissolving 10.0 g of hydroxypropyl methyl cellulose (methoxyl group content of 28 to 30%, hydroxypropoxyl group content of 7 to 12%, kinematic viscosity of 12.5 to 17.5 mm$^2$/s) (manufactured by Shin-Etsu Chemical Co., Ltd., product name: TC-5S) as a water soluble polymer and 1.0 g of concentrated glycerin as a plasticizer into 90 ml of purified water as a solvent.

The obtained solution was spread onto a polyethylene terephthalate-made framework for film formation by using a baker applicator (manufactured by Imoto Machinery Co., Ltd.). Through-circulation drying was performed on the solvent under 60° C. to remove the solvent. Thus, a film was formed.
(2) Preparation of Active-ingredient-containing Layer A solution was prepared by dissolving 6.0 g of d-chlorpheniramine maleate and 0.6 g of belladonna alkaloid as active ingredients, 30.0 g of hydroxypropyl methyl cellulose (methoxyl group content of 28.0 to 30.0%, hydroxypropoxyl group content of 7.0 to 12.0%, kinematic viscosity of 2.5 to 3.5 mm$^2$/s) (manufactured by Shin-Etsu Chemical Co., Ltd., product name: H.P.M.C TC-5E) as a water soluble polymer, 12.0 g of a sucrose fatty acid ester as an emulsifier, 3.0 g of acesulfame potassium and 3.0 g of aspartame as sweeteners, 6.6 g of L-menthol as a corrective and 18.0 g of concentrated glycerin as a plasticizer into 120.0 g of an aqueous solution of high ethanol concentration (ethanol concentration: 80% by volume) as a solvent.

The obtained solution was spread onto the framework on which the active-ingredient-free layer was formed by using the baker applicator (manufactured by Imoto Machinery Co., Ltd.). Through-circulation drying was performed on the solvent under 60° C. to remove the solvent. Thus, a film was formed.
(3) Preparation of Second Active-ingredient-free Layer A solution was prepared by dissolving 10.0 g of hydroxypropyl methyl cellulose (methoxyl group content of 28 to 30%, hydroxypropoxyl group content of 7 to 12%, kinematic viscosity of 12.5 to 17.5 mm$^2$/s) (manufactured by Shin-Etsu Chemical Co., Ltd., product name: TC-5S) as a water soluble polymer and 1.0 g of concentrated glycerin as a plasticizer into 90 ml of purified water as a solvent.

The obtained solution was spread onto the framework on which the first active-ingredient-free layer and the active-ingredient-containing layer were formed by using the baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.14 mm (the active-ingredient-containing layer: 0.13 mm, the first active-ingredient-free layer: 0.005 mm and the second active-ingredient-free layer: 0.005 mm). The content of the active ingredients was 6.5% by mass relative to the total mass of the film preparation. The content of the water soluble polymer was 49.4% by mass relative to the total mass of the film preparation. In addition, the total content of the active ingredients and the water soluble polymer in the obtained active-ingredient-containing layer was 55.9% by mass relative to the total mass of the active-ingredient-containing layer.

Comparative Example 1-E

Monolayer Film Preparation Including Crystalline Cellulose as Disintegrating Agent A film preparation having a monolayer structure formed of only one active-ingredient-containing layer was prepared.
(1) Preparation of Active-ingredient-containing Layer A solution was prepared by dissolving 6.0 g of d-chlorpheniramine maleate and 0.6 g of belladonna alkaloid as active ingredients, 30.0 g of hydroxypropyl methyl cellulose (methoxyl group content of 28.0 to 30.0%, hydroxypropoxyl group content of 7.0 to 12.0%, kinematic viscosity of 2.5 to 3.5 mm$^2$/s) (manufactured by Shin-Etsu Chemical Co., Ltd., product name: H.P.M.C TC-5E) as a water soluble polymer, 12.0 g of a sucrose fatty acid ester as an emulsifier, 3.0 g of acesulfame potassium and 3.0 g of aspartame as sweeteners, 6.6 g of L-menthol as a corrective, 18.0 g of concentrated glycerin as a plasticizer and 56.7 g of a mixture of crystalline cellulose and carboxymethyl cellulose sodium (compounding ratio (mass basis) of 80:20, kinematic viscosity of 30 to 100 mPa·s) (manufactured by Asahi Kasei Chemicals Corporation, product name: Ceolus RC-A591NF) as a water-nonfoamable disintegrating agent into 120.0 g of an aqueous solution of high ethanol concentration (ethanol concentration: 80% by volume) as a solvent.

The obtained solution was spread onto a framework for film formation by using a baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.14 mm. The content of the active ingredients was 4.9% by mass relative to the total mass of the film preparation. The content of the water soluble polymer was 22.1% by mass relative to the total mass of the film preparation. In addition, the total content of the active ingredients and the water soluble polymer in the obtained active-ingredient-containing layer was 26.9% by mass relative to the total mass of the active-ingredient-containing layer.

Example 1-G

Two-layer Film Preparation Including Water-foamable Disintegrating Agent as Disintegrating Agent A film preparation having a two-layer structure formed of one active-ingredient-containing layer and one active-ingredient-free layer was prepared.
(1) Preparation of Active-ingredient-free Layer A solution was prepared by dissolving 10.0 g of hydroxypropyl methyl cellulose (methoxyl group content of 28 to 30%, hydroxypropoxyl group content of 7 to 12%, kinematic viscosity of 12.5 to 17.5 mm$^2$/s) (manufactured by Shin-Etsu Chemical Co., Ltd., product name: TC-5S) as a water soluble polymer and 1.0 g of concentrated glycerin as a plasticizer into 90 ml of purified water as a solvent.

The obtained solution was spread onto a polyethylene terephthalate-made framework for film formation by using a baker applicator (manufactured by Imoto Machinery Co., Ltd.). Through-circulation drying was performed on the solvent under 60° C. to remove the solvent. Thus, a film was formed.
(2) Preparation of Active-ingredient-containing Layer A solution was prepared by dissolving 6.0 g of d-chlorpheniramine maleate and 0.6 g of belladonna alkaloid as active ingredients, 30.0 g of hydroxypropyl cellulose (hydroxypropoxyl group content of 53.4 to 77.5%, kinematic viscosity of 2.0 to 2.9 mPa·s) (manufactured by Nippon Soda Co. Ltd., product name: HPC-SSL) as a water soluble polymer, 12.0 g of a sucrose fatty acid ester as an emulsifier, 3.0 g of acesulfame potassium and 3.0 g of aspartame as sweeteners, 6.6 g of L-menthol as a corrective, 18.0 g of concentrated glycerin as a plasticizer and 12.0 g of citric acid (manufactured by Iwata Chemical Co., Ltd.) and 48.0 g of calcium carbonate (manufactured by Nitto Funka Kogyo K.K.) as water-foamable disintegrating agents into 120.0 g of an aqueous solution of high ethanol concentration (ethanol concentration: 100% by volume) as a solvent.

The obtained solution was spread onto the framework on which the active-ingredient-free layer was formed by using the baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.14 mm (the active-ingredient-containing layer: 0.13 mm, the active-ingredient-free layer: 0.01 mm). The content of the active ingredients was 4.4% by mass relative to the total mass of the film preparation. The content of the water soluble polymer was 26.6% by mass relative to the total mass of the film preparation. In addition, the total content of the active ingredients and the water soluble polymer in the obtained active-ingredient-containing layer was 31.0% by mass relative to the total mass of the active-ingredient-containing layer.

Comparative Example 1-H

Monolayer Film Preparation Including Water-foamable Disintegrating Agent as Disintegrating Agent A film preparation having a monolayer structure formed of only one active-ingredient-containing layer was prepared.
(1) Preparation of Active-ingredient-containing Layer A solution was prepared by dissolving 6.0 g of d-chlorpheniramine maleate and 0.6 g of belladonna alkaloid as active ingredients, 30.0 g of hydroxypropyl methyl cellulose (methoxyl group content of 28.0 to 30.0%, hydroxypropoxyl group content of 7.0 to 12.0%, kinematic viscosity of 2.5 to 3.5 mm$^2$/s) (manufactured by Shin-Etsu Chemical Co., Ltd., product name: H.P.M.C TC-5E) as a water soluble polymer, 12.0 g of a sucrose fatty acid ester as an emulsifier, 3.0 g of acesulfame potassium and 3.0 g of aspartame as sweeteners, 6.6 g of L-menthol as a corrective, 18.0 g of concentrated glycerin as a plasticizer and 12.0 g of citric acid (manufactured by Iwata Chemical Co., Ltd.) and 48.0 g of calcium carbonate (manufactured by Nitto Funka Kogyo K.K.) as water-foamable disintegrating agents into 120.0 g of an aqueous solution of high ethanol concentration (ethanol concentration: 80% by volume) as a solvent.

The obtained solution was spread onto a framework for film formation by using a baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.14 mm. The content of the active ingredients was 4.7% by mass relative to the total mass of the film preparation. The content of the water soluble polymer was 21.6% by mass relative to the total mass of the film preparation. In addition, the total content of the active ingredients and the water soluble polymer in the obtained active-ingredient-containing layer was 26.3% by mass relative to the total mass of the active-ingredient-containing layer.

Test Example 1

Evaluation of Rapid Solubility and Flexibility of Film Preparations in Examples 1 and Comparative Examples 1

The rapid solubility and flexibility of each film preparation were evaluated according to the following procedures, respectively. The results are shown in Table 1.
Evaluation of Rapid Solubility A dissolution time (in second) was measured in accordance with a second method (Paddle Method) of Dissolution Test in Japanese Pharmacopoeia. The testing conditions were: the number of rotations: 50 rpm, temperature: 37±0.5° C., quantity of testing liquid: 900 ml, and testing liquid: purified water. The rapid solubility was evaluated in accordance with following criteria based on the dissolution time.

o: having a rapid solubility: the dissolution time was within 40 seconds x: not having a rapid solubility: the dissolution time was longer than 40 seconds
Evaluation of Flexibility The evaluation was made by a folding test. Specifically, the film preparation was folded to 180° by hand with the middle points (positions being 15.0 mm away from both edges) of the major axis as a fold line. After the hand was released, the state of the film preparation was evaluated in accordance with the following criteria.

o: after folding, the film was not split.

Δ: after folding, the film was not split, but a crack was generated.

x: after folding, the film was split.

TABLE 1

Rapid solubility and flexibility of film preparations

| | Rapid solubility (dissolution time) | Flexibility |
|---|---|---|
| Example 1-A | o (12 seconds) | o |
| Comparative Example 1-B | x (63 seconds) | o |
| Comparative Example 1-C | x (62 seconds) | o |
| Comparative Example 1-D | x (98 seconds) | o |
| Comparative Example 1-E | o (10 seconds) | Δ |
| Example 1-G | o (29 seconds) | o |
| Comparative Example 1-H | o (21 seconds) | Δ |

Table 1 shows that both rapid solubility and flexibility were achieved at the same time in Examples 1-A and 1-G.

Example 2-A

Two-layer Film Preparation Including Active Ingredient in High Content

A film preparation having a two-layer structure formed of one active-ingredient-containing layer and one active-ingredient-free layer was prepared.
(1) Preparation of Active-ingredient-free Layer A solution was prepared by dissolving 10.0 g of hydroxypropyl methyl cellulose (methoxyl group content of 28 to 30%, hydroxypropoxyl group content of 7 to 12%, kinematic viscosity of 12.5 to 17.5 mm$^2$/s) (manufactured by Shin-Etsu Chemical Co., Ltd., product name: TC-5S) as a water soluble polymer and 1.0 g of concentrated glycerin as a plasticizer into 90 ml of purified water as a solvent.

The obtained solution was spread onto a polyethylene terephthalate-made framework for film formation by using a baker applicator (manufactured by Imoto Machinery Co., Ltd.). Through-circulation drying was performed on the solvent under 60° C. to remove the solvent. Thus, a film was formed.
(2) Preparation of Active-ingredient-containing Layer A solution was prepared by dissolving 100.0 g of coenzyme Q10 as an active ingredient, 30.0 g of hydroxypropyl cellulose (hydroxypropoxyl group content of 53.4 to 77.5%, kinematic viscosity of 2.0 to 2.9 mPa·s), Nippon Soda Co., Ltd., product name: HPC-SSL, as a water soluble polymer, 1.0 g of acesulfame potassium and 1.0 g of aspartame as correctives, 30.0 g of concentrated glycerin as a plasticizer, and 12.0 g of citric acid (manufactured by Iwata Chemical Co., Ltd.) and 48.0 g of calcium carbonate (manufactured by Nitta Funka Kogyo K.K.) as water-foamable disintegrating agents into 170.0 g of an ethanol solution (ethanol concentration: 100% by volume) as a solvent.

The obtained solution was spread onto the framework on which the active-ingredient-free layer was formed by using the baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.45 mm (the active-ingredient-containing layer: 0.44 mm, the active-ingredient-free layer: 0.01 mm). The content of the active ingredient was 42.9% by mass relative to the total mass of the film preparation. The content of the water soluble polymer was 17.2% by mass relative to the total mass of the film preparation. In addition, the total content of the active ingredient and the water soluble polymer in the obtained active-ingredient-containing layer was 60.1% by mass relative to the total mass of the active-ingredient-containing layer. A1

Comparative Example 2-B

Comparative Example 2-B

Two-layer Film Preparation Including Active Ingredient in High Content, but not Including Disintegrating Agent A film preparation having a two-layer structure formed of one active-ingredient-containing layer not including a disintegrating agent and one active-ingredient-free layer was prepared.
(1) Preparation of Active-ingredient-free Layer A solution was prepared by dissolving 10.0 g of hydroxypropyl methyl cellulose (methoxyl group content of 28 to 30%, hydroxypropoxyl group content of 7 to 12%, kinematic TC-5S) as a water soluble polymer and 1.0 g of concentrated glycerin as a plasticizer into 90 ml of purified water as a solvent.

The obtained solution was spread onto a polyethylene terephthalate-made framework for film formation by using a baker applicator (manufactured by Imoto Machinery Co., Ltd.). Through-circulation drying was performed on the solvent under 60° C. to remove the solvent. Thus, a film was formed.
(2) Preparation of Active-ingredient-containing Layer A solution was prepared by dissolving 100.0 g of coenzyme Q10 as an active ingredient, 30.0 g of hydroxypropyl cellulose (hydroxypropoxyl group content of 53.4 to 77.5%, kinematic viscosity of 2.0 to 2.9 mPa·s), Nippon Soda Co., Ltd., product name: HPC-SSL, as a water soluble polymer, 1.0 g of acesulfame potassium and 1.0 g of aspartame as correctives and 30.0 g of concentrated glycerin as a plasticizer into 170.0 g of an ethanol solution (ethanol concentration: 100% by volume) as a solvent.

The obtained solution was spread onto the framework on which the active- ingredient-free layer was formed by using the baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.45 mm (the active-ingredient-containing layer: 0.44 mm, the active-ingredient-free layer: 0.01 mm). The content of the active ingredient was 57.8% by mass relative to the total mass of the film preparation. The content of the water soluble polymer was 23.1% by mass relative to the total mass of the film preparation. In addition, the total content of the active ingredient and the water soluble polymer in the obtained active-ingredient-containing layer was 80.9% by mass relative to the total mass of the active-ingredient-containing layer.

Comparative Example 2-C

Monolayer Film Preparation Including Active Ingredient in High Content, but not Including Disintegrating Agent A film preparation having a monolayer structure formed of only one active-ingredient-containing layer was prepared.
(1) Preparation of Active-ingredient-containing Layer A solution was prepared by dissolving 100.0 g of coenzyme Q10 as an active ingredient, 30.0 g of hydroxypropyl cellulose (hydroxypropoxyl group content of 53.4 to 77.5%, kinematic viscosity of 2.0 to 2.9 mPa·s), Nippon Soda Co., Ltd., product name: HPC-SSL, as a water soluble polymer, 1.0 g of acesulfame potassium and 1.0 g of aspartame as correctives and 30.0 g of concentrated glycerin as a plasticizer into 170.0 g of an ethanol solution (ethanol concentration: 100% by volume) as a solvent.

The obtained solution was spread onto a framework for film formation by using a baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.45 mm. The content of the active ingredient was 61.7% by mass relative to the total mass of the film preparation. The content of the water soluble polymer was 18.5% by mass relative to the total mass of the film preparation. In addition, the total content of the active ingredient and the water soluble polymer in the obtained active-ingredient-containing layer was 80.2% by mass relative to the total mass of the active-ingredient-containing layer.

Comparative Example 2-D

Three-layer Film Preparation Including Active Ingredient in High Content, but not Including Disintegrating Agent A film preparation having a three-layer structure formed of one active-ingredient-containing layer not including a disintegrating agent and two active-ingredient-free layers was prepared.
(1) Preparation of First Active-ingredient-free Layer A solution was prepared by dissolving 10.0 g of hydroxypropyl methyl cellulose (methoxyl group content of 28 to 30%, hydroxypropoxyl group content of 7 to 12%, kinematic viscosity of 12.5 to 17.5 mm$^2$/s) (manufactured by Shin-Etsu Chemical Co., Ltd., product name: TC-5S) as a water soluble polymer and 1.0 g of concentrated glycerin as a plasticizer into 90 ml of purified water as a solvent.

The obtained solution was spread onto a polyethylene terephthalate-made framework for film formation by using a baker applicator (manufactured by Imoto Machinery Co., Ltd.). Through-circulation drying was performed on the solvent under 60° C. to remove the solvent. Thus, a film was formed.
(2) Preparation of Active-ingredient-containing Layer A solution was prepared by dissolving 100.0 g of coenzyme Q10 as an active ingredient, 30.0 g of hydroxypropyl cellulose (hydroxypropoxyl group content of 53.4 to 77.5%, kinematic viscosity of 2.0 to 2.9 mPa·s), Nippon Soda Co., Ltd., product name: HPC-SSL, as a water soluble polymer, 1.0 g of acesulfame potassium and 1.0 g of aspartame as correctives and 30.0 g of concentrated glycerin as a plasticizer into 170.0 g of an ethanol solution (ethanol concentration: 100% by volume) as a solvent.

The obtained solution was spread onto the framework on which the active-ingredient-free layer was formed by using the baker applicator (manufactured by Imoto Machinery Co., Ltd.). Through-circulation drying was performed on the solvent under 60° C. to remove the solvent. Thus, a film was formed.
(3) Preparation of Second Active-ingredient-free Layer A solution was prepared by dissolving 10.0 g of hydroxypropyl methyl cellulose (methoxyl group content of 28 to 30%, hydroxypropoxyl group content of 7 to 12%, kinematic viscosity of 12.5 to 17.5 mm$^2$/s) (manufactured by Shin-Etsu Chemical Co., Ltd., product name: TC-5S) as a water soluble polymer and 1.0 g of concentrated glycerin as a plasticizer into 90 ml of purified water as a solvent.

The obtained solution was spread onto the framework on which the first active-ingredient-free layer and the active-ingredient-containing layer were formed by using the baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.45 mm (the active-ingredient-containing layer: 0.44 mm, the first active-ingredient-free layer: 0.005 mm and the second active-ingredient-free layer: 0.005 mm). The content of the active ingredient was 54.3% by mass relative to the total mass of the film preparation. The content of the water soluble polymer was 27.2% by mass relative to the total mass of the film preparation. In addition, the total content of the active ingredient and the water soluble polymer in the obtained active-ingredient-containing layer was 81.5% by mass relative to the total mass of the active-ingredient-containing layer.

Comparative Example 2-F

Monolayer Film Preparation Including Active Ingredient in High Content

A film preparation formed of only one active-ingredient-containing layer was prepared.
(1) Preparation of Active-ingredient-containing Layer A solution was prepared by dissolving 100.0 g of coenzyme Q10 as an active ingredient, 30.0 g of hydroxypropyl cellulose (hydroxypropoxyl group content of 53.4 to 77.5%, kinematic viscosity of 2.0 to 2.9 mPa·s), Nippon Soda Co., Ltd., product name: HPC-SSL, as a water soluble polymer, 1.0 g of acesulfame potassium and 1.0 g of aspartame as correctives, 30.0 g of concentrated glycerin as a plasticizer, and 10.0 g of a mixture of crystalline cellulose and carboxymethyl cellulose sodium (compounding ratio (mass basis) of 80:20, kinematic viscosity of 30 to 100 mPa·s) (manufactured by Asahi Kasei Chemicals Corporation, product name: Ceolus RC-A591NF) as a water-non-foamable disintegrating agent into 170.0 g of an ethanol solution (ethanol concentration: 100% by volume) as a solvent.

The obtained solution was spread onto a framework for film formation by using a baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.45 mm. The content of the active ingredient was 58.1% by mass relative to the total mass of the film preparation. The content of the water soluble polymer was 17.4% by mass relative to the total mass of the film preparation. In addition, the total content of the active ingredient and the water soluble polymer in the obtained active-ingredient-containing layer was 75.6% by mass relative to the total mass of the active-ingredient-containing layer.

Comparative Example 2-H

Monolayer Film Preparation Including Active Ingredient in High Content

A film preparation having a monolayer structure formed of only one active-ingredient-containing layer was prepared.

(1) Preparation of Active-ingredient-containing Layer

A solution was prepared by dissolving 100.0 g of coenzyme Q10 as an active ingredient, 30.0 g of hydroxypropyl cellulose (hydroxypropoxyl group content of 53.4 to 77.5%, kinematic viscosity of 2.0 to 2.9 mPa·s), Nippon Soda Co., Ltd., product name: HPC-SSL, as a water soluble polymer, 1.0 g of acesulfame potassium and 1.0 g of aspartame as correctives, 30.0 g of concentrated glycerin as a plasticizer, and 12.0 g of citric acid (manufactured by Iwata Chemical Co., Ltd.) and 48.0 g of calcium carbonate (manufactured by Nitta Funka Kogyo K.K.) as water-foamable disintegrating agents into 170.0 g of an ethanol solution (ethanol concentration: 100% by volume) as a solvent.

The obtained solution was spread onto a framework for film formation by using a baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.45 mm. The content of the active ingredient was 45.0% by mass relative to the total mass of the film preparation. The content of the water soluble polymer was 13.5% by mass relative to the total mass of the film preparation. In addition, the total content of the active ingredient and the water soluble polymer in the obtained active-ingredient-containing layer was 58.6% by mass relative to the total mass of the active-ingredient-containing layer.

Example 2-I

Three-layer Film Preparation Including Active Ingredient in High Content

A film preparation having a three-layer structure formed of one active-ingredient-containing layer and two active-ingredient-free layer was prepared to A film.

(1) Preparation of First Active-ingredient-free Layer

A solution was prepared by dissolving 10.0 g of hydroxypropyl methyl cellulose (methoxyl group content of 28 to 30%, hydroxypropoxyl group content of 7 to 12%, kinematic viscosity of 12.5 to 17.5 mm2/s) (manufactured by Shin-Etsu Chemical Co., Ltd., product name: TC-5S) as a water soluble polymer and 1.0 g of concentrated glycerin as a plasticizer into 90 ml of purified water as a solvent.

The obtained solution was spread onto a polyethylene terephthalate-made framework for film formation by using a baker applicator (manufactured by Imoto Machinery Co., Ltd.). Through-circulation drying was performed on the solvent under 60° C. to remove the solvent. Thus, a film was formed.

(2) Preparation of Active-ingredient-containing Layer

A solution was prepared by dissolving 100.0 g of coenzyme Q10 as an active ingredient, 30.0 g of hydroxypropyl cellulose (hydroxypropoxyl group content of 53.4 to 77.5%, kinematic viscosity of 2.0 to 2.9 mPa·s), Nippon Soda Co., Ltd., product name: HPC-SSL, as a water soluble polymer, 1.0 g of acesulfame potassium and 1.0 g of aspartame as correctives, 30.0 g of concentrated glycerin as a plasticizer, and 12.0 g of citric acid (manufactured by Iwata Chemical Co., Ltd.) and 48.0 g of calcium carbonate (manufactured by Nitta Funka Kogyo K.K.) as water-foamable disintegrating agents into 170.0 g of an ethanol solution (ethanol concentration: 100% by volume) as a solvent.

The obtained solution was spread onto the framework on which the active-ingredient-free layer was formed by using the baker applicator (manufactured by Imoto Machinery Co., Ltd.). Through-circulation drying was performed on the solvent under 60° C. to remove the solvent. Thus, a film was formed.

(3) Preparation of Second Active-ingredient-free Layer

A solution was prepared by dissolving 10.0 g of hydroxypropyl methyl cellulose (methoxyl group content of 28 to 30%, hydroxypropoxyl group content of 7 to 12%, kinematic viscosity of 12.5 to 17.5 mm$^2$/s) (manufactured by Shin-Etsu Chemical Co., Ltd., product name: TC-5S) as a water soluble polymer and 1.0 g of concentrated glycerin as a plasticizer into 90 ml of purified water as a solvent.

The obtained solution was spread onto the framework on which the first active- ingredient-free layer and the active-ingredient-containing layer were formed by using the baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.45 mm (the active-ingredient-containing layer: 0.44 mm, the first active-ingredient-free layer: 0.005 mm and the second active-ingredient-free layer: 0.005 mm). The content of the active ingredient was 41.0% by mass relative to the total mass of the film preparation. The content of the water soluble polymer was 20.5% by mass relative to the total mass of the film preparation. In addition, the total content of the active ingredient and the water soluble polymer in the obtained active-ingredient-containing layer was 61.5% by mass relative to the total mass of the active-ingredient-containing layer.

Test Example 2

Evaluation of Rapid Solubility and Flexibility of Film Preparations in Examples 2 and Comparative Examples 2

The rapid solubility and flexibility of each film preparation were evaluated according to the same procedures in Test Example 1. The results are shown in Table 2.

TABLE 2

| | Rapid solubility and flexibility of film preparations | |
|---|---|---|
| | Rapid solubility (dissolution time) | Flexibility |
| Example 2-A | o (16 seconds) | o |
| Comparative Example 2-B | x (290 seconds) | o |
| Comparative Example 2-C | x (142 seconds) | x |

TABLE 2-continued

Rapid solubility and flexibility of film preparations

|  | Rapid solubility (dissolution time) | Flexibility |
| --- | --- | --- |
| Comparative Example 2-D | x (328 seconds) | o |
| Comparative Example 2-F | x (176 seconds) | x |
| Comparative Example 2-H | o (18 seconds) | x |
| Example 2-I | o (38 seconds) | o |

Table 2 shows that both rapid solubility and flexibility were achieved at the same time in Examples 2-A and 2-I although the active ingredients were included in high content.

In following Examples 3 to 14, film preparations including various active ingredients (drugs) were prepared.

Example 3

Two-Layer Film Preparation Including D-chlorpheniramine Maleate and Scopolamine Hydrobromide as Active Ingredients A film preparation having a two-layer structure formed of one active-ingredient-containing layer and one active-ingredient-free layer was prepared.

(1) Preparation of Active-ingredient-free Layer

A solution was prepared by dissolving 10.0 g of hydroxypropyl methyl cellulose (methoxyl group content of 28 to 30%, hydroxypropoxyl group content of 7 to 12%, kinematic viscosity of 12.5 to 17.5 mm$^2$/s) (manufactured by Shin-Etsu Chemical Co., Ltd., product name: TC-5S) as a water soluble polymer and 1.0 g of concentrated glycerin as a plasticizer into 90 ml of purified water as a solvent.

The obtained solution was spread onto a polyethylene terephthalate-made framework for film formation by using a baker applicator (manufactured by Imoto Machinery Co., Ltd.). Through-circulation drying was performed on the solvent under 60° C. to remove the solvent. Thus, a film was formed.

(2) Preparation of Active-ingredient-containing Layer

A solution was prepared by dissolving 3.0 g of d-chlorpheniramine maleate and 0.18 g of scopolamine hydrobromide as active ingredients, 30.0 g of hydroxypropyl methyl cellulose (methoxyl group content of 28.0 to 30.0%, hydroxypropoxyl group content of 7.0 to 12.0%, kinematic viscosity of 2.5 to 3.5 mm$^2$/s) (manufactured by Shin-Etsu Chemical Co., Ltd., product name: H.P.M.C TC-5E) as a water soluble polymer, 12.0 g of a sucrose fatty acid ester as an emulsifier, 3.0 g of acesulfame potassium and 3.0 g of aspartame as sweeteners, 6.6 g of L-menthol as a corrective, 18.0 g of concentrated glycerin as a plasticizer and 56.7 g of a mixture of crystalline cellulose and carboxymethyl cellulose sodium (compounding ratio (mass basis) 80:20, kinematic viscosity of 30 to 100 mPa·s) (manufactured by Asahi Kasei Chemicals Corporation, product name: Ceolus RC-A591NF) as a water-non-foamable disintegrating agent into 120.0 g of an aqueous solution of high ethanol concentration (ethanol concentration: 80% by volume) as a solvent.

The obtained solution was spread onto the framework on which the active-ingredient-free layer was formed by using the baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.14 mm (the active-ingredient-containing layer: 0.13 mm, the active-ingredient-free layer: 0.01 mm). The content of the active ingredients was 2.2% by mass relative to the total mass of the film preparation. The content of the water soluble polymer was 27.9% by mass relative to the total mass of the film preparation. In addition, the total content of the active ingredients and the water soluble polymer in the obtained active-ingredient-containing layer was 30.1% by mass relative to the total mass of the active-ingredient-containing layer.

Example 4

Two-layer Film Preparation Including tipepidine hibenzate, trimetoquinol hydrochloride and d-chlorpheniramine maleate as Active Ingredients A film preparation having a two-layer structure formed of one active-ingredient-containing layer and one active-ingredient-free layer was prepared.

(1) Preparation of Active-ingredient-free Layer

A solution was prepared by dissolving 10.0 g of hydroxypropyl methyl cellulose (methoxyl group content of 28 to 30%, hydroxypropoxyl group content of 7 to 12%, kinematic viscosity of 12.5 to 17.5 mm$^2$/s) (manufactured by Shin-Etsu Chemical Co., Ltd., product name: TC-5S) as a water soluble polymer and 1.0 g of concentrated glycerin as a plasticizer into 90 ml of purified water as a solvent.

The obtained solution was spread onto a polyethylene terephthalate-made framework for film formation by using a baker applicator (manufactured by Imoto Machinery Co., Ltd.). Through-circulation drying was performed on the solvent under 60° C. to remove the solvent. Thus, a film was formed.

(2) Preparation of Active-ingredient-containing Layer

A solution was prepared by dissolving 24.9 g of tipepidine hibenzate, 1.8 g of trimetoquinol hydrochloride and 1.8 g of d-chlorpheniramine maleate as active ingredients, 30.0 g of hydroxypropyl methyl cellulose (methoxyl group content of 28.0 to 30.0%, hydroxypropoxyl group content of 7.0 to 12.0%, kinematic viscosity of 2.5 to 3.5 mm$^2$/s) (manufactured by Shin-Etsu Chemical Co., Ltd., product name: H.P.M.C TC-5E) as a water soluble polymer, 12.0 g of a sucrose fatty acid ester as an emulsifier, 3.0 g of acesulfame potassium and 3.0 g of aspartame as sweeteners, 6.6 g of L-menthol as a corrective, 18.0 g of concentrated glycerin as a plasticizer and 56.7 g of a mixture of crystalline cellulose and carboxymethyl cellulose sodium (compounding ratio (mass basis) of 80:20, kinematic viscosity of 30 to 100 mPa·s) (manufactured by Asahi Kasei Chemicals Corporation, product name: Ceolus RC-A591NF) as a water-non-foamable disintegrating agent into 120.0 g of an aqueous solution of high ethanol concentration (ethanol concentration: 80% by volume) as a solvent.

The obtained solution was spread onto the framework on which the active-ingredient-free layer was formed by using the baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.14 mm (the active-ingredient-containing layer: 0.13 mm, the active-ingredient-free layer: 0.01 mm). The content of the active ingredients was 16.9% by mass relative to the total mass of the film preparation. The content of the water soluble polymer was 23.7% by mass relative to the total mass of the film preparation. In addition, the total content of the active ingredients and the water soluble polymer in the obtained active-ingredient-containing layer was 40.6% by mass relative to the total mass of the active-ingredient-containing layer.

Example 5

Two-layer Film Preparation Including dextromethorphan phenolphthalinate as Active Ingredient A film preparation having a two-layer structure formed of one active-ingredient-containing layer and one active-ingredient-free layer was prepared.

(1) Preparation of Active-ingredient-free Layer

A solution was prepared by dissolving 10.0 g of hydroxypropyl methyl cellulose (methoxyl group content of 28 to 30%, hydroxypropoxyl group content of 7 to 12%, kinematic viscosity of 12.5 to 17.5 mm$^2$/s) (manufactured by Shin-Etsu Chemical Co., Ltd., product name: TC-5S) as a water soluble polymer and 1.0 g of concentrated glycerin as a plasticizer into 90 ml of purified water as a solvent.

The obtained solution was spread onto a polyethylene terephthalate-made framework for film formation by using a baker applicator (manufactured by Imoto Machinery Co., Ltd.). Through-circulation drying was performed on the solvent under 60° C. to remove the solvent. Thus, a film was formed.

(2) Preparation of Active-ingredient-containing Layer

A solution was prepared by dissolving 30.0 g of dextromethorphan phenolphthalinate as an active ingredient, 30.0 g of hydroxypropyl methyl cellulose (methoxyl group content of 28.0 to 30.0%, hydroxypropoxyl group content of 7.0 to 12.0%, kinematic viscosity of 2.5 to 3.5 mm$^2$/s) (manufactured by Shin-Etsu Chemical Co., Ltd., product name: H.P.M.C TC-5E) as a water soluble polymer, 12.0 g of a sucrose fatty acid ester as an emulsifier, 3.0 g of acesulfame potassium and 3.0 g of aspartame as sweeteners, 6.6 g of L-menthol as a corrective, 18.0 g of concentrated glycerin as a plasticizer and 56.7 g of a mixture of crystalline cellulose and carboxymethyl cellulose sodium (compounding ratio (mass basis) of 80:20, kinematic viscosity of 30 to 100 mPa·s) (manufactured by Asahi Kasei Chemicals Corporation, product name: Ceolus RC-A591NF) as a water-non-foamable disintegrating agent into 120.0 g of an aqueous solution of high ethanol concentration (ethanol concentration: 80% by volume) as a solvent.

The obtained solution was spread onto the framework on which the active-ingredient-free layer was formed by using the baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.14 mm (the active-ingredient-containing layer: 0.13 mm, the active-ingredient-free layer: 0.01 mm). The content of the active ingredient was 17.6% by mass relative to the total mass of the film preparation. The content of the water soluble polymer was 23.5% by mass relative to the total mass of the film preparation. In addition, the total content of the active ingredient and the water soluble polymer in the obtained active-ingredient-containing layer was 41.1% by mass relative to the total mass of the active-ingredient-containing layer.

Example 6

Two-layer Film Preparation Including Famotidine as Active Ingredient

A film preparation having a two-layer structure formed of one active-ingredient-containing layer and one active-ingredient-free layer was prepared.

(1) Preparation of Active-ingredient-free Layer

A solution was prepared by dissolving 10.0 g of hydroxypropyl methyl cellulose (methoxyl group content of 28 to 30%, hydroxypropoxyl group content of 7 to 12%, kinematic viscosity of 12.5 to 17.5 mm$^2$/s) (manufactured by Shin-Etsu Chemical Co., Ltd., product name: TC-5S) as a water soluble polymer and 1.0 g of concentrated glycerin as a plasticizer into 90 ml of purified water as a solvent.

The obtained solution was spread onto a polyethylene terephthalate-made framework for film formation by using a baker applicator (manufactured by Imoto Machinery Co., Ltd.). Through-circulation drying was performed on the solvent under 60° C. to remove the solvent. Thus, a film was formed.

(2) Preparation of Active-ingredient-containing Layer

A solution was prepared by dissolving 30.0 g of famotidine as an active ingredient, 30.0 g of hydroxypropyl methyl cellulose (methoxyl group content of 28.0 to 30.0%, hydroxypropoxyl group content of 7.0 to 12.0%, kinematic viscosity of 2.5 to 3.5 mm$^2$/s) (manufactured by Shin-Etsu Chemical Co., Ltd., product name: H.P.M.C TC-5E) as a water soluble polymer, 12.0 g of a sucrose fatty acid ester as an emulsifier, 3.0 g of acesulfame potassium and 3.0 g of aspartame as sweeteners, 6.6 g of L-menthol as a corrective, 18.0 g of concentrated glycerin as a plasticizer and 56.7 g of a mixture of crystalline cellulose and carboxymethyl cellulose sodium (compounding ratio (mass basis) of 80:20, kinematic viscosity of 30 to 100 mPa·s) (manufactured by Asahi Kasei Chemicals Corporation, product name: Ceolus RC-A591NF) as a water-non-foamable disintegrating agent into 120.0 g of an aqueous solution of high ethanol concentration (ethanol concentration: 80% by volume) as a solvent.

The obtained solution was spread onto the framework on which the active-ingredient-free layer was formed by using the baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.14 mm (the active-ingredient-containing layer: 0.13 mm, the active-ingredient-free layer: 0.01 mm). The content of the active ingredient was 17.6% by mass relative to the total mass of the film preparation. The content of the water soluble polymer was 23.5% by mass relative to the total mass of the film preparation. In addition, the total content of the active ingredient and the water soluble polymer in the obtained active-ingredient-containing layer was 41.1% by mass relative to the total mass of the active-ingredient-containing layer.

Example 7

Two-layer Film Preparation Including loperamide hydrochloride as Active Ingredient A film preparation having a two-layer structure formed of one active-ingredient-containing layer and one active-ingredient-free layer was prepared.

(1) Preparation of Active-ingredient-free Layer

A solution was prepared by dissolving 10.0 g of hydroxypropyl methyl cellulose (methoxyl group content of 28 to 30%, hydroxypropoxyl group content of 7 to 12%, kinematic viscosity of 12.5 to 17.5 mm$^2$/s) (manufactured by Shin-Etsu Chemical Co., Ltd., product name: TC-5S) as a water soluble polymer and 1.0 g of concentrated glycerin as a plasticizer into 90 ml of purified water as a solvent.

The obtained solution was spread onto a polyethylene terephthalate-made framework for film formation by using a baker applicator (manufactured by Imoto Machinery Co., Ltd.). Through-circulation drying was performed on the solvent under 60° C. to remove the solvent. Thus, a film was formed.

(2) Preparation of Active-ingredient-containing Layer

A solution was prepared by dissolving 3.0 g of loperamide hydrochloride as an active ingredient, 30.0 g of hydroxypropyl methyl cellulose (methoxyl group content of 28.0 to 30.0%, hydroxypropoxyl group content of 7.0 to 12.0%, kinematic viscosity of 2.5 to 3.5 mm$^2$/s) (manufactured by Shin-Etsu Chemical Co., Ltd., product name: H.P.M.C TC-5E) as a water soluble polymer, 12.0 g of a sucrose fatty acid ester as an emulsifier, 3.0 g of acesulfame potassium and 3.0 g of aspartame as sweeteners, 6.6 g of L-menthol as a corrective, 18.0 g of concentrated glycerin as a plasticizer and 56.7 g of a mixture of crystalline cellulose and carboxymethyl cellulose sodium (compounding ratio (mass basis) of 80:20, kinematic viscosity of 30 to 100 mPa·s) (manufactured by Asahi Kasei Chemicals Corporation, product name: Ceolus RC-A591NF) as a water-non-foamable disintegrating agent into 120.0 g of an aqueous solution of high ethanol concentration (ethanol concentration: 80% by volume) as a solvent.

The obtained solution was spread onto the framework on which the active-ingredient-free layer was formed by using the baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.14 mm (the active-ingredient-containing layer: 0.13 mm, the active-ingredient-free layer: 0.01 mm). The content of the active ingredient was 2.1% by mass relative to the total mass of the film preparation. The content of the water soluble polymer was 27.9% by mass relative to the total mass of the film preparation. In addition, the total content of the active ingredient and the water soluble polymer in the obtained active-ingredient-containing layer was 30.0% by mass relative to the total mass of the active-ingredient-containing layer.

Example 8

Two-layer Film Preparation Including fexofenadine hydrochloride as Active Ingredient A film preparation having a two-layer structure formed of one active-ingredient-containing layer and one active-ingredient-free layer was prepared.

(1) Preparation of Active-ingredient-free Layer

A solution was prepared by dissolving 10.0 g of hydroxypropyl methyl cellulose (methoxyl group content of 28 to 30%, hydroxypropoxyl group content of 7 to 12%, kinematic viscosity of 12.5 to 17.5 mm$^2$/s) (manufactured by Shin-Etsu Chemical Co., Ltd., product name: TC-5S) as a water soluble polymer and 1.0 g of concentrated glycerin as a plasticizer into 90 ml of purified water as a solvent.

The obtained solution was spread onto a polyethylene terephthalate-made framework for film formation by using a baker applicator (manufactured by Imoto Machinery Co., Ltd.). Through-circulation drying was performed on the solvent under 60° C. to remove the solvent. Thus, a film was formed.

(2) Preparation of Active-ingredient-containing Layer

A solution was prepared by dissolving 1.0 g of fexofenadine hydrochloride as an active ingredient, 30.0 g of hydroxypropyl methyl cellulose (methoxyl group content of 28.0 to 30.0%, hydroxypropoxyl group content of 7.0 to 12.0%, kinematic viscosity of 2.5 to 3.5 mm$^2$/s) (manufactured by Shin-Etsu Chemical Co., Ltd., product name: H.P.M.C TC-5E) as a water soluble polymer, 1.0 g of α-cyclodextrin (Nihon Shokuhin Kako Co., Ltd.) as a masking reagent, 12.0 g of a sucrose fatty acid ester as an emulsifier, 3.0 g of acesulfame potassium and 3.0 g of aspartame as sweeteners, 6.6 g of L-menthol as a corrective, 18.0 g of concentrated glycerin as a plasticizer and 56.7 g of a mixture of crystalline cellulose and carboxymethyl cellulose sodium (compounding ratio (mass basis) of 80:20, kinematic viscosity of 30 to 100 mPa·s) (manufactured by Asahi Kasei Chemicals Corporation, product name: Ceolus RC-A591NF) as a water-non-foamable disintegrating agent into 120.0 g of an aqueous solution of high ethanol concentration (ethanol concentration: 80% by volume) as a solvent.

The obtained solution was spread onto the framework on which the active-ingredient-free layer was formed by using the baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.14 mm (the active-ingredient-containing layer: 0.13 mm, the active-ingredient-free layer: 0.01 mm). The content of the active ingredient was 0.7% by mass relative to the total mass of the film preparation. The content of the water soluble polymer was 28.1% by mass relative to the total mass of the film preparation. In addition, the total content of the active ingredient and the water soluble polymer in the obtained active-ingredient-containing layer was 28.8% by mass relative to the total mass of the active-ingredient-containing layer.

Example 9

Two-layer Film Preparation Including Cetirizine Hydrochloride as Active Ingredient A film preparation having a two-layer structure formed of one active-ingredient-containing layer and one active-ingredient-free layer was prepared.

(1) Preparation of Active-ingredient-free Layer

A solution was prepared by dissolving 10.0 g of hydroxypropyl methyl cellulose (methoxyl group content of 28 to 30%, hydroxypropoxyl group content of 7 to 12%, kinematic viscosity of 12.5 to 17.5 mm$^2$/s) (manufactured by Shin-Etsu Chemical Co., Ltd., product name: TC-5S) as a water soluble polymer and 1.0 g of concentrated glycerin as a plasticizer into 90 ml of purified water as a solvent.

The obtained solution was spread onto a polyethylene terephthalate-made framework for film formation by using a baker applicator (manufactured by Imoto Machinery Co., Ltd.). Through-circulation drying was performed on the solvent under 60° C. to remove the solvent. Thus, a film was formed.

(2) Preparation of Active-ingredient-containing Layer

A solution was prepared by dissolving 1.0 g of cetirizine hydrochloride as an active ingredient, 30.0 g of hydroxypropyl methyl cellulose (methoxyl group content of 28.0 to 30.0%, hydroxypropoxyl group content of 7.0 to 12.0%, kinematic viscosity of 2.5 to 3.5 mm$^2$/s) (manufactured by Shin-Etsu Chemical Co., Ltd., product name: H.P.M.C TC-5E) as a water soluble polymer, 1.0 g of β-cyclodextrin (Nihon Shokuhin Kako Co., Ltd.) as a masking reagent, 12.0 g of a sucrose fatty acid ester as an emulsifier, 3.0 g of acesulfame potassium and 3.0 g of aspartame as sweeteners, 6.6 g of L-menthol as a corrective, 18.0 g of concentrated glycerin as a plasticizer and 56.7 g of a mixture of crystalline cellulose and carboxymethyl cellulose sodium (compounding ratio (mass basis) of 80:20, kinematic viscosity of 30 to 100 mPa·s) (manufactured by Asahi Kasei Chemicals Corporation, product name: Ceolus RC-A591NF) as a water-non-foamable disintegrating agent into 120.0 g of an aqueous solution of high ethanol concentration (ethanol concentration: 80% by volume) as a solvent.

The obtained solution was spread onto the framework on which the active-ingredient-free layer was formed by using the baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.14 mm (the active-ingredient-containing layer: 0.13 mm, the active-ingredient-free layer: 0.01 mm). The content of the active ingredient was 0.7% by mass relative to the total mass of the film preparation. The content of the water soluble polymer was 28.1% by mass relative to the total mass of the film preparation. In addition, the total content of the active ingredient and the water soluble polymer in the obtained active-ingredient-containing layer was 28.8% by mass relative to the total mass of the active-ingredient-containing layer.

Example 10

Two-layer Film Preparation Including Mequitazine as Active Ingredient

A film preparation having a two-layer structure formed of one active-ingredient-containing layer and one active-ingredient-free layer was prepared.

(1) Preparation of Active-ingredient-free Layer

A solution was prepared by dissolving 12.3 g of hydroxypropyl methyl cellulose (methoxyl group content of 28 to 30%, hydroxypropoxyl group content of 7 to 12%, kinematic viscosity of 12.5 to 17.5 mm$^2$/s) (manufactured by Shin-Etsu Chemical Co., Ltd., product name: TC-5S) as a water soluble polymer and 18.0 g of concentrated glycerin as a plasticizer into 100 ml of purified water as a solvent.

The obtained solution was spread onto a polyethylene terephthalate-made framework for film formation by using a baker applicator (manufactured by Imoto Machinery Co., Ltd.). Through-circulation drying was performed on the solvent under 60° C. to remove the solvent. Thus, a film was formed.

(2) Preparation of Active-ingredient-containing Layer

A solution was prepared by dissolving 1.0 g of mequitazine as an active ingredient, 30.0 g of hydroxypropyl methyl cellulose (methoxyl group content of 28.0 to 30.0%, hydroxypropoxyl group content of 7.0 to 12.0%, kinematic viscosity of 2.5 to 3.5 mm$^2$/s) (manufactured by Shin-Etsu Chemical Co., Ltd., product name: H.P.M.C TC-5E) as a water soluble polymer, 1.0 g of γ-cyclodextrin (Nihon Shokuhin Kako Co., Ltd.) as a masking reagent, 12.0 g of a sucrose fatty acid ester as an emulsifier, 3.0 g of acesulfame potassium and 3.0 g of aspartame as sweeteners, 6.6 g of L-menthol as a corrective, 18.0 g of concentrated glycerin as a plasticizer and 56.7 g of a mixture of crystalline cellulose and carboxymethyl cellulose sodium (compounding ratio (mass basis) of 80:20, kinematic viscosity of 30 to 100 mPa·s) (manufactured by Asahi Kasei Chemicals Corporation, product name: Ceolus RC-A591NF) as a water-non-foamable disintegrating agent into 120.0 g of an aqueous solution of high ethanol concentration (ethanol concentration: 80% by volume) as a solvent.

The obtained solution was spread onto the framework on which the active-ingredient-free layer was formed by using the baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.14 mm (the active-ingredient-containing layer: 0.13 mm, the active-ingredient-free layer: 0.01 mm). The content of the active ingredient was 0.7% by mass relative to the total mass of the film preparation. The content of the water soluble polymer was 28.1% by mass relative to the total mass of the film preparation. In addition, the total content of the active ingredient and the water soluble polymer in the obtained active-ingredient-containing layer was 28.8% by mass relative to the total mass of the active-ingredient-containing layer.

Example 11

Two-layer Film Preparation Including Diphenhydramine Hydrochloride as Active Ingredient A film preparation having a two-layer structure formed of one active-ingredient-containing layer and one active-ingredient-free layer was prepared.

(1) Preparation of Active-ingredient-free Layer

A solution was prepared by dissolving 10.0 g of hydroxypropyl methyl cellulose (methoxyl group content of 28 to 30%, hydroxypropoxyl group content of 7 to 12%, kinematic viscosity of 12.5 to 17.5 mm$^2$/s) (manufactured by Shin-Etsu Chemical Co., Ltd., product name: TC-5S) as a water soluble polymer and 1.0 g of concentrated glycerin as a plasticizer into 90 ml of purified water as a solvent.

The obtained solution was spread onto a polyethylene terephthalate-made framework for film formation by using a baker applicator (manufactured by Imoto Machinery Co., Ltd.). Through-circulation drying was performed on the solvent under 60° C. to remove the solvent. Thus, a film was formed.

(2) Preparation of Active-ingredient-containing Layer 125.0 g of diphenhydramine hydrochloride as an active ingredient and 375.0 g of stearyl alcohol (Kao Corporation) as a masking reagent were melted by heating at 80° C. Thereafter, the solution was sprayed by using the spray drier DL-41, and then quickly cooled to prepare a micromatrix having a particle diameter of 50 μm.

A solution was prepared by dissolving 100.0 g of the obtained micromatrix, 30.0 g of hydroxypropyl cellulose (hydroxypropoxyl group content of 53.4 to 77.5%, kinematic viscosity of 2.0 to 2.9 mPa·s), Nippon Soda Co., Ltd., product name: HPC-SSL, as a water soluble polymer, 12.0 g of a sucrose fatty acid ester as an emulsifier, 3.0 g of acesulfame potassium and 3.0 g of aspartame as sweeteners, 6.6 g of L-menthol as a corrective, 18.0 g of concentrated glycerin as a plasticizer, and 12.0 g of citric acid (manufactured by Iwata Chemical Co., Ltd.) and 48.0 g of calcium carbonate (manufactured by Nitto Funka Kogyo K.K.) as water-foamable disintegrating agents into 170.0 g of an ethanol solution (ethanol concentration: 100% by volume) as a solvent.

The obtained solution was spread onto the framework on which the active-ingredient-free layer was formed by using the baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.45 mm (the active-ingredient-containing layer: 0.44 mm, the activeingredient-free layer: 0.01 mm). The content of the active ingredient was 41.1% by mass relative to the total mass of the film preparation. The content of the water soluble polymer was 16.4% by mass relative to the total mass of the film preparation. In addition, the total content of the active ingredient and the water soluble polymer in the obtained active-ingredient-containing layer was 57.5% by mass relative to the total mass of the active-ingredient-containing layer.

Example 12

Two-layer Film Preparation Including Dextromethorphan Hydrobromide as Active Ingredient A film preparation having a two-layer structure formed of one active-ingredient-containing layer and one active-ingredient-free layer was prepared.
(1) Preparation of Active-ingredient-free Layer A solution was prepared by dissolving 10.0 g of hydroxypropyl methyl cellulose (methoxyl group content of 28 to 30%, hydroxypropoxyl group content of 7 to 12%, kinematic viscosity of 12.5 to 17.5 mm$^2$/s) (manufactured by Shin-Etsu Chemical Co., Ltd., product name: TC-5S) as a water soluble polymer and 1.0 g of concentrated glycerin as a plasticizer into 90 ml of purified water as a solvent.

The obtained solution was spread onto a polyethylene terephthalate-made framework for film formation by using a baker applicator (manufactured by Imoto Machinery Co., Ltd.). Through-circulation drying was performed on the solvent under 60° C. to remove the solvent. Thus, a film was formed.
(2) Preparation of Active-ingredient-containing Layer 150.0 g of dextromethorphan hydrobromide as an active ingredient and 600.0 g of stearyl alcohol (Kao Corporation) as a masking reagent were melted by heating at 80° C. Thereafter, the solution was sprayed by using the spray drier DL-41, and then quickly cooled to prepare a micromatrix having a particle diameter of 50 µm.

A solution was prepared by dissolving 100.0 g of the obtained micromatrix, 30.0 g of hydroxypropyl cellulose (hydroxypropoxyl group content of 53.4 to 77.5%, kinematic viscosity of 2.0 to 2.9 mPa·s), Nippon Soda Co., Ltd., product name: HPC-SSL, as a water soluble polymer, 12.0 g of a sucrose fatty acid ester as an emulsifier, 3.0 g of acesulfame potassium and 3.0 g of aspartame as sweeteners, 6.6 g of L-menthol as a corrective, 18.0 g of concentrated glycerin as a plasticizer, and 12.0 g of citric acid (manufactured by Iwata Chemical Co., Ltd.) and 48.0 g of calcium carbonate (manufactured by Nitto Funka Kogyo K.K.) as water-foamable disintegrating agents into 170.0 g of an ethanol solution (ethanol concentration: 100% by volume) as a solvent.

The obtained solution was spread onto the framework on which the active-ingredient-free layer was formed by using the baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.45 mm (the active-ingredient-containing layer: 0.44 mm, the active-ingredient-free layer: 0.01 mm). The content of the active ingredient was 41.1% by mass relative to the total mass of the film preparation. The content of the water soluble polymer was 16.4% by mass relative to the total mass of the film preparation. In addition, the total content of the active ingredient and the water soluble polymer in the obtained active-ingredient-containing layer was 57.5% by mass relative to the total mass of the active-ingredient-containing layer.

Example 13

Two-layer Film Preparation Including Fluvoxamine Maleate as Active Ingredient

A film preparation having a two-layer structure formed of one active-ingredient-containing layer and one active-ingredient-free layer was prepared.
(1) Preparation of Active-ingredient-free Layer A solution was prepared by dissolving 10.0 g of hydroxypropyl methyl cellulose (methoxyl group content of 28 to 30%, hydroxypropoxyl group content of 7 to 12%, kinematic viscosity of 12.5 to 17.5 mm$^2$/s) (manufactured by Shin-Etsu Chemical Co., Ltd., product name: TC-5S) as a water soluble polymer and 1.0 g of concentrated glycerin as a plasticizer into 90 ml of purified water as a solvent.

The obtained solution was spread onto a polyethylene terephthalate-made framework for film formation by using a baker applicator (manufactured by Imoto Machinery Co., Ltd.). Through-circulation drying was performed on the solvent under 60° C. to remove the solvent. Thus, a film was formed.
(2) Preparation of Active-ingredient-containing Layer 250.0 g of fluvoxamine maleate as an active ingredient as well as 100.0 g of ion-exchange resin AMBERLITE IRP88 (ROHM AND HAAS FRANCE S.A.S.) and 650.0 g of stearic acid (NOF CORPORATION) as masking reagents were melted by heating at 80° C. Thereafter, the solution was sprayed by using the spray drier DL-41, and then quickly cooled to prepare a micromatrix having a particle diameter of 50 µm.

A solution was prepared by dissolving 100.0 g of the obtained micromatrix, 30.0 g of hydroxypropyl cellulose (hydroxypropoxyl group content of 53.4 to 77.5%, kinematic viscosity of 2.0 to 2.9 mPa·s), Nippon Soda Co., Ltd., product name: HPC-SSL, as a water soluble polymer, 12.0 g of a sucrose fatty acid ester as an emulsifier, 3.0 g of acesulfame potassium and 3.0 g of aspartame as sweeteners, 6.6 g of L-menthol as a corrective, 18.0 g of concentrated glycerin as a plasticizer, and 12.0 g of citric acid (manufactured by Iwata Chemical Co., Ltd.) and 48.0 g of calcium carbonate (manufactured by Nitto Funka ////////////////////////////////////// A1 Kogyo K.K.) as water-foamable disintegrating agents into 170.0 g of an ethanol solution (ethanol concentration: 100% by volume) as a solvent.

The obtained solution was spread onto the framework on which the active-ingredient-free layer was formed by using the baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.45 mm (the active-ingredient-containing layer: 0.44 mm, the active-ingredient-free layer: 0.01 mm). The content of the active ingredient was 41.1% by mass relative to the total mass of the film preparation. The content of the water soluble polymer was 16.4% by mass relative to the total mass of the film preparation. In addition, the total content of the active ingredient and the water soluble polymer in the obtained active-ingredient-containing layer was 57.5% by mass relative to the total mass of the active-ingredient-containing layer.

Example 14

Two-Layer Film Preparation Including Phenylephrine Hydrochloride as Active Ingredient A film preparation having a two-layer structure formed of one active-ingredient-containing layer and one active-ingredient-free layer was prepared.

(1) Preparation of Active-Ingredient-Free Layer

A solution was prepared by dissolving 10.0 g of hydroxypropyl methyl cellulose (methoxyl group content of 28 to 30%, hydroxypropoxyl group content of 7 to 12%, kinematic viscosity of 12.5 to 17.5 mm$^2$/s) (manufactured by Shin-Etsu Chemical Co., Ltd., product name: TC-5S) as a water soluble polymer and 1.0 g of concentrated glycerin as a plasticizer into 90 ml of purified water as a solvent.

The obtained solution was spread onto a polyethylene terephthalate-made framework for film formation by using a baker applicator (manufactured by Imoto Machinery Co., Ltd.). Through-circulation drying was performed on the solvent under 60° C. to remove the solvent. Thus, a film was formed.

(2) Preparation of Active-Ingredient-Containing Layer 100.0 g of phenylephrine hydrochloride as an active ingredient and 400.0 g of stearyl alcohol (NOF CORPORATION) as a masking reagent were melted by heating at 80° C. Thereafter, the solution was sprayed by using the spray drier DL-41, and then quickly cooled to prepare a micromatrix having a particle diameter of 50 μm.

A solution was prepared by dissolving 100.0 g of the obtained micromatrix, 30.0 g of hydroxypropyl cellulose (hydroxypropoxyl group content of 53.4 to 77.5%, kinematic viscosity of 2.0 to 2.9 mPa·s), Nippon Soda Co., Ltd., product name: HPC-SSL, as a water soluble polymer, 12.0 g of a sucrose fatty acid ester as an emulsifier, 3.0 g of acesulfame potassium and 3.0 g of aspartame as sweeteners, 6.6 g of L-menthol as a corrective, 18.0 g of concentrated glycerin as a plasticizer, and 12.0 g of citric acid (manufactured by Iwata Chemical Co., Ltd.) and 48.0 g of calcium carbonate (manufactured by Nitto Funka Kogyo K.K.) as water-foamable disintegrating agents into 170.0 g of an ethanol solution (ethanol concentration: 100% by volume) as a solvent.

The obtained solution was spread onto the framework on which the active-ingredient-free layer was formed by using the baker applicator (manufactured by Imoto Machinery Co., Ltd.). Through-circulation drying was performed on the solvent under 60° C. to remove the solvent. Thus, a film was formed.

The formed film was released from the framework and cut to obtain a rectangular film preparation having a minor axis of 20.0 mm, a major axis of 30.0 mm and a thickness of 0.45 mm (the active-ingredient-containing layer: 0.44 mm, the active-ingredient-free layer: 0.01 mm). The content of the active ingredient was 41.1% by mass relative to the total mass of the film preparation. The content of the water soluble polymer was 16.4% by mass relative to the total mass of the film preparation. In addition, the total content of the active ingredient and the water soluble polymer in the obtained active-ingredient-containing layer was 57.5% by mass relative to the total mass of the active-ingredient-containing layer.

Test Example 3

Evaluation of Rapid Solubility and Flexibility of the Film Preparations in Example 3 to 14

The rapid solubility and flexibility of each film preparation were evaluated according to the same procedures in Test Example 1. The results are shown in Table 3.

TABLE 3

Rapid solubility and flexibility of film preparations

|  | Rapid solubility (dissolution time) | Flexibility |
|---|---|---|
| Example 3 | ○ (12 seconds) | ○ |
| Example 4 | ○ (15 seconds) | ○ |
| Example 5 | ○ (18 seconds) | ○ |
| Example 6 | ○ (18 seconds) | ○ |
| Example 7 | ○ (12 seconds) | ○ |
| Example 8 | ○ (12 seconds) | ○ |
| Example 9 | ○ (10 seconds) | ○ |
| Example 10 | ○ (10 seconds) | ○ |
| Example 11 | ○ (21 seconds) | ○ |
| Example 12 | ○ (23 seconds) | ○ |
| Example 13 | ○ (19 seconds) | ○ |
| Example 14 | ○ (20 seconds) | ○ |

Table 3 shows that both rapid solubility and flexibility were achieved at the same time in any of Examples 3 to 14.

INDUSTRIAL APPLICABILITY

A film preparation of the present invention can be used for drugs and foods depending on the type of active ingredients.

The invention claimed is:

1. A rapidly soluble film preparation comprising:
an active-ingredient-containing layer consisting of
an active ingredient,
a water soluble polymer selected from the group consisting of methyl cellulose, hydroxypropyl cellulose and hydroxypropyl methyl cellulose,
a disintegrating agent which is a mixture of crystalline cellulose and carboxymethyl cellulose sodium,
a plasticizer,
one or more substances selected from the group consisting of an emulsifier, a sweetener, a corrective, a masking reagent and an aromatizer; and
an active-ingredient-free layer comprising the plasticizer and a component selected from the group consisting of methyl cellulose and hydroxypropyl methyl cellulose,
wherein a content of the active ingredient is from 0.1% by mass to 75.0% by mass of a total mass of the film preparation,
a total content of the active ingredient and the water soluble polymer in the active-ingredient-containing layer is from 15.0% by mass to 95.0% by mass of a total mass of the active-ingredient-containing layer, and
a content of the water soluble polymer in the film preparation is from 5.0 to 35.0% by mass relative to the total mass of the film preparation,
wherein the emulsifier is selected from the group consisting of alkylbenzene sulfonate, carrageenan, carboxy vinyl polymers, guar gum, glycerin fatty acid esters, sucrose fatty acid esters, stearic acid, lanolin, egg-yolk lecithin, cetanol, sorbitan fatty acid esters, soybean lecithin, sorbitan trioleate, pectin, polyoxyethylene hydrogenated castor oil, sodium lauryl sulfate and lauromacrogol;
wherein the sweetener is selected from the group consisting of acesulfame potassium, aspartame, dipotassium glycyrrhizinate, saccharin, sodium saccharin, thaumatin and stevia;
wherein the corrective is selected from the group consisting of adipic acid, ascorbic acid, citric acid, tartaric acid, tannic acid, fumaric acid, malic acid, methyl salicylate and L-menthol;

wherein the plasticizer is selected from the group consisting of Triethyl citrate, glycerin, triacetin, propylene glycol, polyoxyethylene (105) polyoxypropylene (5) glycol, polysorbate, macrogol, glyceryl monostearate and mannitol;

wherein the masking agent is selected from the group consisting of a cyclodextrin and an ion-exchange resin;

wherein the aromatizer is selected from the group consisting of fennel oil, orange oil, chamomile oil, camphor, cinnamon oil, salvia oil, spearmint oil, clove oil, mentha oil, vanillin, peppermint extract, bergamot oil, borneol, eucalyptus oil, lavender oil, lemon oil, rose oil and Roman chamomile oil;

wherein a content of the plasticizer in both of the active-ingredient containing layer and the active-ingredient-free layer is from 11.16% by mass to 22.28% by mass of a total mass of the rapidly soluble film preparation; and wherein a content of the disintegrating agent is from 33.29% by mass to 39.85% by mass of a total mass of the rapidly soluble film preparation.

2. The rapidly soluble film preparation according to claim 1, which has a three-layer structure in which the active-ingredient-free layers exist on each side of the active-ingredient-containing layer.

3. The rapidly soluble film preparation according to claim 1, which has a two-layer structure in which the active-ingredient-free layer exists on one side of the active-ingredient-containing layer.

4. The rapidly soluble film preparation according to claim 1, wherein the mixture of crystalline cellulose and carboxymethyl cellulose sodium is a colloidal grade.

5. The rapidly soluble film preparation according to claim 1, which is a film preparation for oral administration.

6. The film preparation according to claim 1, wherein the active ingredient is selected from the group consisting of a sedative hypnotic, an antianxiety drug, an antiepileptic, a rhinitis drug, an antipyretic-analgesic-anti inflammatory drug, an anti-parkinsonian, an antipsychotic, a local anesthetic agent, a cerebral circulation and metabolism ameliorator, an antispasmodic, an antiemetic, a cardiotonic drug, an antiarrhythmic, a diuretic, an antihypertensive, a vasoconstrictor, a vasodilator, a hypolipidemic drug, a respiratory stimulant, an antitussive, an expectorant, an antitussive and expectorant drug, a bronchodilator, a gargle, an antidiarrheal, an intestinal regulator, an antiulcer drug, a stomachic, an antacid, a laxative, a cholagogue, an analeptic, an antipodagric, an anti-diabetic drug, an antibiotic, an antimicrobial, an osteoporosis drug, a skeletal muscle relaxant, an antirheumatic agent, a hormonal drug, an alkaloidal narcotic, a blood coagulation inhibitor, an antineoplastic, an antihistaminic and an antiallergic.

7. The film preparation according to claim 1, wherein the water soluble polymer in the active-ingredient-containing layer is hydroxypropyl methyl cellulose and the active-ingredient-free layer comprises hydroxypropyl methyl cellulose.

* * * * *